(12) United States Patent
Bolli et al.

(10) Patent No.: US 7,951,794 B2
(45) Date of Patent: May 31, 2011

(54) THIOPHENE DERIVATIVES

(75) Inventors: Martin Bolli, Allschwil (CH); David Lehmann, Basel (CH); Boris Mathys, Pratteln (CH); Claus Mueller, Weil Am Rhein (DE); Jörg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 253 days.

(21) Appl. No.: 11/993,563

(22) PCT Filed: Jun. 20, 2006

(86) PCT No.: PCT/IB2006/051990
§ 371 (c)(1),
(2), (4) Date: Dec. 21, 2007

(87) PCT Pub. No.: WO2006/137019
PCT Pub. Date: Dec. 28, 2006

(65) Prior Publication Data
US 2010/0075946 A1 Mar. 25, 2010

(30) Foreign Application Priority Data
Jun. 24, 2005 (WO) ................. PCT/EP2005/006840

(51) Int. Cl.
*A61K 31/00* (2006.01)
(52) U.S. Cl. ................................. 514/210.18
(58) Field of Classification Search .................. None
See application file for complete search history.

(56) References Cited

U.S. PATENT DOCUMENTS

| | | | |
|---|---|---|---|
| 2004/0058894 A1 | 3/2004 | Doherty et al. | |
| 2006/0293252 A1 | 12/2006 | Glombik et al. | |
| 2008/0064740 A1 | 3/2008 | Bolli et al. | |
| 2008/0176926 A1 | 7/2008 | Bolli et al. | |
| 2008/0194670 A1 | 8/2008 | Bolli et al. | |
| 2008/0300294 A1 | 12/2008 | Bolli et al. | |
| 2008/0318955 A1 | 12/2008 | Bolli et al. | |
| 2009/0005421 A1 | 1/2009 | Bolli et al. | |
| 2010/0075946 A1 | 3/2010 | Bolli et al. | |

FOREIGN PATENT DOCUMENTS

| | | |
|---|---|---|
| EP | 0 476 646 | 3/1992 |
| WO | WO-91/15583 A1 | 10/1991 |
| WO | WO-99/46277 A1 | 9/1999 |
| WO | WO-03/014107 A1 | 2/2003 |
| WO | WO 03/062248 | 7/2003 |
| WO | WO 03/062252 | 7/2003 |
| WO | WO-2004/007517 A1 | 1/2004 |
| WO | WO 2004/010949 | 2/2004 |
| WO | WO 2005/014525 * | 2/2005 |
| WO | WO-2005/014525 A2 | 2/2005 |
| WO | WO 2006/010544 | 2/2006 |
| WO | WO 2007/098474 | 8/2007 |

OTHER PUBLICATIONS

Hla, Timothy et al.:"An Abundant Transcript Induced in Differentiating Human Endothelial Cells Encodes a Polypeptide with Structural Similarities to G-protein-coupled Receptors"; The Journal of Biological Chemistry, vol. 265, No. 16, Issue of Jun. 5, pp. 9308-9313, 1990.
Gould, Philip L.: "Salt selection for basic drugs"; International Journal of Pharmaceutics, 33 (1986), pp. 201-217.
Mark Gibson, Editior, Pharmaceutical Preformulation and Formulation, IHS Health Group, Englewood, CO, USA, 2001.
Alfonso R. Gennaro, Editor, Remington: The Science and Practice of Pharmacy, 20th Edition, Philadelphia College of Pharmacy and Science.
Mentzel, M. et al.; "*N*-Methoxy-*N*-methylamides (Weinreb Amides) in Modern Organic Synthesis"; Journal fuer praktische Chemie Chemiker-Zeitung 339 (1997), pp. 517-524.
Singh, J. et al.; "The Growing Synthetic Utility of Weinreb's Amide"; Journal fuer praktische Chemi Chemiker-Zeitung, (Weinheim, Germany), 342 (2000), pp. 340-347.
Khlestkin, Vladimir K. et al.; "Recent Advances in the Application of N,O-Dialkylhydroxylamines in Organic Chemistry"; Current Organic Chemistry, 2003, 7, pp. 967-993.
Gonzalez, Isabel C. et al.; "Novel thiophenes and analogues with anthelmintic activity against *Haemonchus contortus*"; Bioorganic & Medicinal Chemistry Letters 14 (2004) pp. 4037-4043.
Rudolph, M. Jonathan et al.; "Design and Synthesis of 4,5-Disubstituted-thiophene-2-amidines as Potent Urokinase Inhibitors"; Bioorganic & Medicinal Chemistry Letters 12 (2002) pp. 491-495.
Subasinghe, Natlin L. et al.; "Structure-Based Design, Synthesis and SAR of a Novel Series of Thiopheneamidine Urokinase Plasminogen Activator Inhibitors"; Bioorganic & Medicinal Chemistry Letters 11 (2001) pp. 1379-1382.
Thiemann, Thies et al.; "One pot Suzuki coupling—Wittig olefination reactions"; Journal of Chemical Research 2004, November, pp. 723-727.
Xu, Bin et al.; "Acyclic Analogues of Adenosine Bisphosphates as P2Y Receptor Antagonists: Phosphate Substitution Leads to Multiple Pathways of Inhibition of Platelet Aggregation"; Journal of Medical Chemistry, 2002, vol. 45, No. 26, pp. 5694-5709.
U.S. Appl. No. 12/160,520, Bolli, et al.
Vippagunta, S.R., et al., Crystalline Solid, Advanced Drug Delivery Reviews, vol. 48, pp. 3-26, (2001).
Guillory, J. K., Generation of Polymorphs, Hydrates, Solvates, and Amorphous Solids, Polymorphism in Pharmaceutical Solids, (Edited by H.G.Brittain), pp. 1-2, 183-226, (1999) NY: Marcel Dekker, Inc.
Brinkmann V., et al., The Immune Modulator FTY720 Targets Sphingosine 1-Phosphate Receptors, The Journal of Biological Chemistry, vol. 277, No. 24, pp. 21453-21457, (Jun. 14, 2002).
Gavezzotti, A., Are Crystal Structures Predictable?, Accounts of Chemical Research, vol. 27, pp. 309-314 (1994).
Actelion: Company Presentation, Internet Article, Nov. 2005, pp. 23-25.
Aust, H. et al., Oligomers of Alternately Arranged Chalcone Building Blocks, J. Prakt Chem., vol. 341, No. 6, pp. 523-528, (1999) (w/ English translation of same).

* cited by examiner

*Primary Examiner* — Brandon J Fetterolf
*Assistant Examiner* — Craig Ricci
(74) *Attorney, Agent, or Firm* — Hoxie & Associates LLC

(57) ABSTRACT

The invention relates to novel thiophene derivatives, their preparation and their use as pharmaceutically active compounds. Said compounds particularly act as immunosuppressive agents.

16 Claims, No Drawings

THIOPHENE DERIVATIVES

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing one or more compounds of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The following paragraphs provide definitions of the various chemical moieties that make up the compounds according to the invention and are intended to apply uniformly throughout the specification and claims unless an otherwise expressly set out definition provides a broader definition.

Any reference to a compound of Formula (I) is to be understood as referring also to optically pure enantiomers, mixtures of enantiomers such as racemates, diastereomers, mixtures of diastereomers, diastereomeric racemates, and mixtures of diastereomeric racemates, as well as salts (especially pharmaceutically acceptable salts) and solvates (including hydrates) of such compounds, and morphological forms, as appropriate and expedient.

The term lower alkyl, alone or in combination with other groups, means saturated, branched or preferably straight chain groups with one to five carbon atoms, preferably one to three carbon atoms. Examples of lower alkyl groups are methyl, ethyl, n-propyl, iso-propyl, n-butyl, iso-butyl, sec-butyl, tert-butyl, and n-pentyl.

The term lower alkoxy means an R—O group, wherein R is a lower alkyl. Preferred examples of lower alkoxy groups are methoxy, ethoxy, propoxy, iso-propoxy, iso-butoxy, sec-butoxy and tert-butoxy.

The term hydroxy-lower alkoxy means a straight or branched alkoxy chain bearing a hydroxy group whereby there are at least two carbon atoms between the hydroxy group and the oxygen of the lower alkoxy group. Examples of hydroxy-lower alkoxy groups are 2-hydroxy-ethoxy, 3-hydroxy-propoxy, 2-hydroxy-propoxy, 4-hydroxy-butoxy, 3-hydroxy-1-methyl-propoxy, 3-hydroxy-butoxy, etc.

The term lower alkylamino or di-(lower alkyl)amino means an R'—NH— or an R'—NR"— group, respectively, wherein R' and R" are each independently a lower alkyl group. Preferred examples of lower alkylamino or di-(lower alkyl)amino groups are methylamino, ethylamino, N,N-dimethylamino, and N-methyl-N-ethyl-amino.

The term halogen means fluoro, chloro, bromo or iodo, preferably fluoro or chloro.

Salts are preferably the pharmaceutically acceptable salts of the compounds of Formula (I).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or polyacid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of Formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", Int. J. Pharm. (1986), 33, 201-217.

i) The invention relates to novel thiophene derivatives of the Formula (I),

Formula (I)

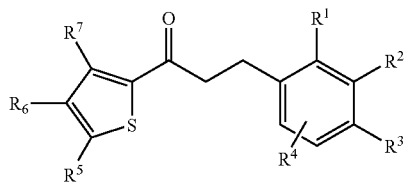

wherein $R^1$ represents hydrogen, lower alkyl, lower alkoxy, or halogen;

$R^2$ represents hydrogen, lower alkyl, lower alkoxy, or halogen;

$R^3$ represents hydrogen, hydroxy-lower alkyl, 2,3-dihydroxypropyl, di-(hydroxy-lower alkyl)-lower alkyl, —CH$_2$—(CH$_2$)$_k$—NR$^{31}$R$^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —CH$_2$—(CH$_2$)$_n$—CONR$^{31}$R$^{32}$, —CO—NHR$^{31}$, 1-(1-(3-carboxy-azetidinyl))-2acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$CH(OH)—CH$_2$—NR$^{31}$R$^{32}$, hydroxy, lower alkoxy, fluoro-lower alkoxy, hydroxy-lower alkoxy, di-(hydroxy-lower alkyl)-lower alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[4-(2-hydroxy-ethyl)-piperazin-1 -yl]-ethoxy, 3-piperazin-1-yl-propoxy, 3-[4-(lower alkyl)piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-(lower alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-

(lower alkyl)piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_nCH(OH)$—$CH_2$—$NHSO_2R^{33}$, —$OCH_2$—$(CH_2)_m$—$NHSO_2R^{33}$, —$OXH_2$—$CH(OH)$—$CH_2$—$NHSO_2R^{33}$, —$CH_2$—$(CH_2)_k$—$NHCOR^{34}$, —$(CH_2)_nCH(OH)$—$CH_2$—$NHCOR^{34}$, —$OCH_2$—$(CH_2)_m$—$NHCOR^{34}$, or —$OCH_2$—$CH(OH)$—$CH_2$—$NHCOR^{34}$;

$R^{31}$ represents hydrogen, methyl, ethyl, 1-propyl, 2-propyl, 2-hydroxyethyl, 2-hydroxy-1-hydroxymethyl-ethyl, 2-lower alkoxyethyl, 3-hydroxypropyl, 3-lower alkoxypropyl, 2-aminoethyl, 2-(lower alkylamino)ethyl, 2-(di-(lower alkyl)amino)ethyl, carboxymethyl, lower alkylcarboxymethyl, 2-carboxyethyl, or 2-(lower alkylcarboxy)ethyl ;

$R^{32}$ represents hydrogen or methyl;

$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents the integer 0, 1, or 2;

$R^4$ represents hydrogen, lower alkyl or halogen;

$R^5$ represents trifluoromethyl, methyl, ethyl, or propyl;

$R^6$ represents phenyl optionally mono- or di-substituted, wherein the substituents are independently selected from methyl, ethyl, trifluoromethyl, halogen and methoxy; or 2-, 3- or 4-pyridyl optionally substituted with methyl or methoxy; and $R^7$ represents hydrogen, or methyl;

and optically pure enantiomers, mixtures of enantiomers such as racemates, diastereomers, mixtures of diastereomers, diastereomeric racemates, and mixtures of diastereomeric racemates, as well as salts and solvates of such compounds, and morphological forms.

ii) A preferred embodiment of the invention relates to thiophene derivatives according to embodiment i), wherein $R^1$ and $R^4$ represent hydrogen, and $R^2$ represents a methyl group.

iii) Another preferred embodiment of the invention relates to thiophene derivatives according to embodiment i), wherein $R^1$ represents hydrogen, and $R^2$ and $R^4$ represent a methyl group, wherein $R^4$ is in the ortho-position with respect to $R^3$.

iv) Another preferred embodiment of the invention relates to thiophene derivatives according to embodiment i), wherein $R^1$ represents hydrogen, $R^2$ represents a methyl group, and $R^4$ represents an ethyl group in the ortho-position with respect to $R^3$.

v) Another preferred embodiment of the invention relates to thiophene derivatives according to embodiment i), wherein $R^1$ represents hydrogen, $R^2$ represents a methyl group, and $R^4$ represents chlorine in the ortho-position with respect to $R^3$.

vi) Another preferred embodiment of the invention relates to thiophene derivatives according to embodiment i), wherein $R^1$ and $R^4$ represent hydrogen, and $R^2$ represents chlorine.

vii) Another preferred embodiment of the invention relates to thiophene derivatives according to embodiment i), wherein $R^1$ represents hydrogen, $R^2$ represents a methoxy group, and $R^4$ represents a chlorine or fluorine in the ortho-position with respect to $R^3$.

viii) Another preferred embodiment of the invention relates to thiophene derivatives according to embodiment i), wherein $R^1$ represents a methoxy group, and $R^2$ and $R^4$ represent hydrogen.

ix) A further preferred embodiment of the invention relates to thiophene derivatives according to any one of the embodiments i) to viii), wherein $R^3$ represents hydrogen, hydroxy-lower alkyl, 2,3-dihydroxypropyl, di-(hydroxy-lower alkyl)-lower alkyl, (azetidine-3-carboxylic acid)-1-yl-methyl, (azetidine-3-carboxylic acid lower alkylester)-1-yl-methyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, —$CH_2$—$(CH_2)_n$—$CONR^{31}R^{32}$, —CO—$NHR^{31}$, —$(CH_2)_nCH(OH)$—$CH_2$—$NR^{31}R^{32}$, lower alkoxy, hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH_2)_m$—$NR^{31}R^{32}$, 2-[(azetidine-3-carboxylic acid)-1-yl]-ethoxy, 2-[(azetidine-3-carboxylic acid lower alkylester)-1-yl]ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)-1-yl] ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—$CH_2$—$CONR^{31}R^{32}$, —$OCH_2$—$CH(OH)$—$CH_2$—$NR^{31}R^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_nCH(OH)$—$CH_2$—$NHSO_2R^{33}$, —$OCH_2$—$(CH_2)_m$—$NHSO_2R^{33}$, —$OCH_2$—$CH(OH)$—$CH_2$—$NHSO_2R^{33}$, —$CH_2$—$(CH_2)_k$—$NHCOR^{34}$, —$(CH_2)_nCH(OH)$—$CH_2$—$NHCOR^{34}$, —$OCH_2$—$(CH_2)_m$—$NHCOR^{34}$, or —$OCH_2$—$CH(OH)$—$CH_2$—$NHCOR^{34}$, wherein $R^{31}$, $R^{32}$, $R^{33}$ and $R^{34}$ are as defined for Formula (I) above.

x) Another further preferred embodiment of the invention relates to thiophene derivatives according to any one of the embodiments i) to viii), wherein $R^3$ represents hydroxy-lower alkyl, 2,3-dihydroxypropyl, di-(hydroxy-lower alkyl)-lower alkyl, (azetidine-3-carboxylic acid)-1-yl-methyl, —CO—$NHR^{31}$, —$(CH_2)_nCH(OH)$—$CH_2$—$NR^{31}R^{32}$, lower alkoxy, hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH_2)_m$—$NR^{31}R^{32}$, 2-amino-3-hydroxy-2-hydroxymethyl-propoxy, —O—$CH_2$—$CONR^{31}R^{32}$, —$OCH_2$—$CH(OH)$—$CH_2$—$NR^{31}R^{32}$, —$NR^{31}R^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$, wherein R$^{31}$, R$^{32}$, R$^{33}$ and R$^{34}$ are as defined for Formula (I) above.

xi) Another further preferred embodiment of the invention relates to thiophene derivatives according to any one of the embodiments i) to viii), wherein R$^3$ represents hydroxy-lower alkyl, 2,3-dihydroxypropyl, di-(hydroxy-lower alkyl)-lower alkyl, —CO—NHR$^{31}$, lower alkoxy, hydroxy-lower alkoxy, di-(hydroxy-lower alkyl)-lower alkoxy, 1-glyceryl, 2-glyceryl, 2-hydroxy-3-methoxy-propoxy, or —O—CH$_2$—CONR$^{31}$R$^{32}$, wherein R$^{31}$ and R$^{32}$ are as defined for Formula (I) above.

xii) A particularly preferred embodiment of the invention relates to thiophene derivatives according to any one of the embodiments i) to xi), wherein R$^5$ represents ethyl.

xiii) Another particularly preferred embodiment of the invention relates to thiophene derivatives according to any one of the embodiments i) to xii), wherein R$^6$ represents an unsubstituted phenyl ring.

xiv) A still further preferred embodiment of the invention relates to thiophene derivatives according to any one of the embodiments i) to xiii), wherein R$^7$ represents hydrogen.

A preferred embodiment of the present invention relates to a compound of Formula
(I), wherein
R$^1$ represents hydrogen;
R$^2$ represents hydrogen, lower alkyl, or lower alkoxy;
R$^3$ represents 2,3-dihydroxypropyl, (azetidine-3-carboxylic acid)-1-yl-methyl, hydroxy, hydroxy-lower alkoxy, 1-glyceryl, —OCH$_2$—(CH$_2$)$_m$—NR$^{31}$R$^{32}$, or —OCH$_2$—CH(OH)—CH$_2$—NR$^{31}$R$^{32}$;
R$^{31}$ represents hydrogen, methyl, or 2-hydroxyethyl;
R$^{32}$ represents hydrogen or methyl;
m represents the integer 1;
R$^4$ represents hydrogen, lower alkyl or halogen;
R$^5$ represents trifluoromethyl, methyl, ethyl, or propyl;
R$^6$ represents phenyl optionally mono- or di-substituted, wherein the substituents are independently selected from methyl, ethyl, trifluoromethyl, halogen and methoxy; or 3-pyridyl; and
R$^7$ represents hydrogen.

Preferred compounds of Formula (I) are those of the Examples given below.

Very preferred compounds of Formula (I) are:
3-[4-((S)-2,3-dihydroxy-propoxy)-3,5-dimethyl-phenyl]-1-(5-ethyl-4-phenyl-thiophen-2-yl)-propan-1-one,
3-[4(S)-2,3-dihydroxy-propoxy)-3,5-dimethyl-phenyl]-1-(5-ethyl-4-(2-methyl-phenyl)-thiophen-2-yl)-propan-1-one, and
3-[4-((S)-2,3-dihydroxy-propoxy)-3,5-dimethyl-phenyl]-1-(4-phenyl-5-propyl-thiophen-2-yl)-propan-1-one.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Preferably, the diseases or disorders to be prevented or treated with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a patient a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimization procedures.

Compounds of the Formula (I) of the present invention can be prepared according to the general sequence of reactions outlined below. Only a few of the synthetic possibilities leading to compounds of Formula (I) are described.

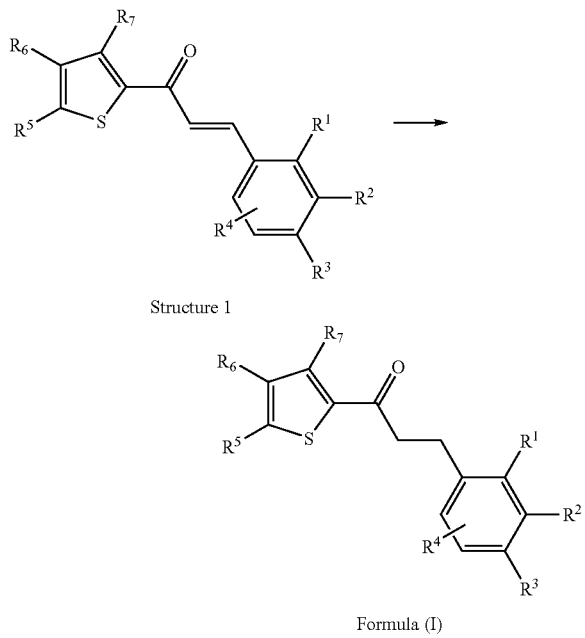

Structure 1

Formula (I)

The compounds of Formula (I) may be prepared by reacting a compound of Structure 1 with hydrogen in the presence of a catalyst such as Pd/C, Pt/C, PtO$_2$, etc. in a solvent such as ethanol, methanol, THF, etc. The compounds of Structure 1 may be prepared by reacting a compound of Structure 2 with a compound of Structure 3 in a solvent such as methanol, ethanol, isopropanol, toluene, etc. in the presence of a base such as KOH, NaOH, NaOMe, NaOEt, potassium tert. butylate, or an acid such as HCl.

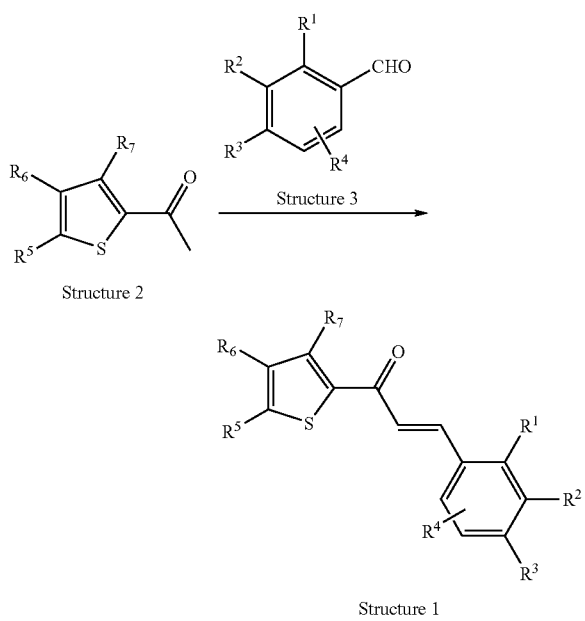

Structure 2

Structure 3

Structure 1

The compounds of Formula (I) in addition may be prepared by reacting a compound of Structure 4 with a compound of Structure 5 under Grignard conditions, preferably at temperatures below room temperature. The Grignard reagent of Structure 5 is prepared according to standard methodology. The functional groups present in the residues $R^1$ to $R^4$ may require temporary protection or may even be introduced in additional steps that follow the Grignard reaction.

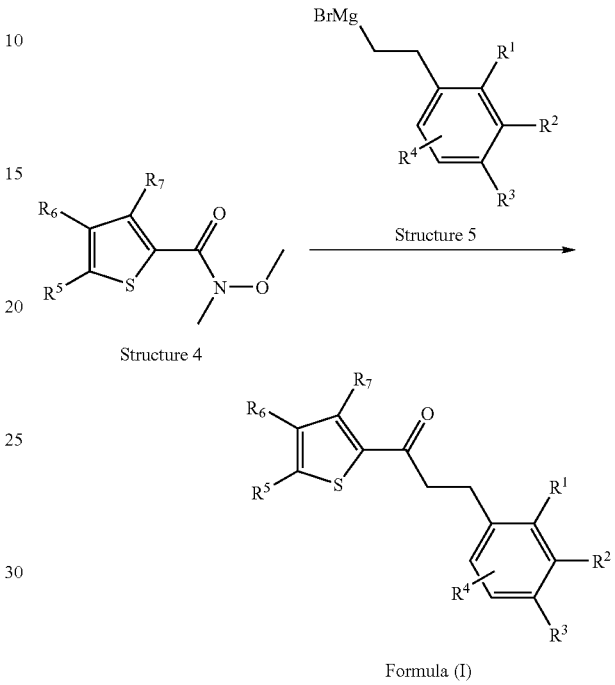

Structure 4

Structure 5

Formula (I)

The Weinreb amide compound of Structure 4 is prepared by treating a compound of Structure 6 with N,O-dimethylhydroxylamine hydrochloride in the presence of a coupling reagent such as EDC, DCC, TBTU, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, Current Organic Chemistry 7 (2003), 967-993).

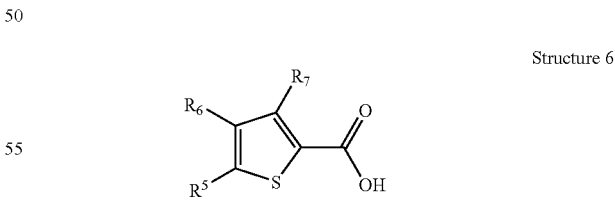

Structure 6

The compounds of Structure 2 may be prepared by treating a compound of Structure 6 with MeLi in a solvent such as diethyl ether, THF, or dioxane, at temperatures between −20 and 50° C. Alternatively, a compound of Structure 2 may be prepared by reacting a compound of Structure 4 with methylmagnesium bromide.

The compounds of Structure 6 are either commercially available or are prepared according to or in analogy to known procedures (e.g. WO 03/014107; I. C. Gonzalez, L. N. Davis, Ch. K. Smith, Bioorg. Med. Chem. Lett. 14 (2004) 4037-4043; M. J. Rudolph et al. Bioorg. Med. Chem. Lett. 12 (2002) 491-495; N. L.

Subasinghe et al. *Bioorg. Med. Chem. Lett.* 11(2001) 1379-1382 and literature cited therein; T. Thiemann, M. Watanabe, Y. Tanaka, S. Mataka, *J. Chem. Res.* 2004, 723-727).

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 µm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

| Abbreviations (as used herein) | |
| --- | --- |
| approx. | approximately |
| aq. | aqueous |
| atm | atmosphere |
| BSA | bovine serum albumin |
| Bu | butyl |
| CC | column chromatography |
| DCC | dicyclohexyl carbodiimide |
| DCM | dichloromethane |
| DIPEA | diisopropyl-ethylamine, Hünig's base, ethyl-diisopropyl-amine |
| DMF | dimethylformamide |
| DMSO | dimethylsulfoxide |
| EA | ethyl acetate |
| EDC | N-(3-dimethylaminopropyl)-N'-ethyl-carbodiimide |
| Et | ethyl |
| h | hour(s) |
| HPLC | high performance liquid chromatography |
| LC-MS | liquid chromatography - mass spectrometry |
| Me | methyl |
| min | minute(s) |
| MPLC | medium pressure liquid chromatography |
| OAc | acetate |
| PdCl$_2$(dppf) | dichloro[1,1'-bis(diphenylphosphino)ferrocene]palladium (II) |
| Ph | phenyl |
| prep. | preparative |
| TBTU | 2-(1H-benzotriazole-1-yl)-1,2,3,3-tetramethyluronium tetrafluoroborate |
| THF | tetrahydrofuran |
| rt | room temperature |
| sat. | saturated |
| S1P | sphingosine 1-phosphate |
| TLC | thin layer chromatography |
| $t_R$ | retention time |

Methanesulfonic acid 2,2-dimethyl[1,3]dioxan-5-ylmethyl ester

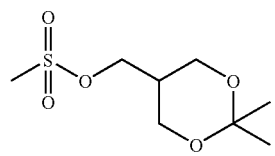

The title compound is prepared following the procedures given in B. Xu, A. Stephens, G. Kirschenheuter, A. F. Greslin, X. Cheng, J. Sennelo, M. Cattaneo, M.

L. Zighetti, A. Chen, S.-A. Kim, H. S. Kim, N. Bischofberger, G. Cook, K. A. Jacobson, *J. Med. Chem.* 45 (2002) 5694-5709.

Example 1

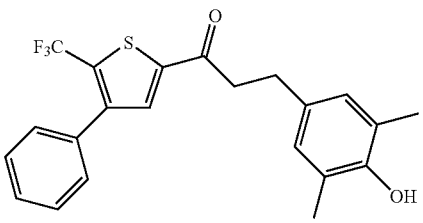

a) At 0° C., DMF (4.3 mL) is carefully treated with phosphoroxychloride (2.8 mL) and the mixture is stirred at rt for 20 min before 1,1,1-trifluoro-3-phenyl-propan-2-one (1.55 mL, 10 mmol) is slowly added. The reaction mixture is stirred for 2 h at 45° C. and 18 h at rt, diluted with sat. aq. Na-acetate solution (20 mL) and water (40 mL) and extracted with diethyl ether. The organic phase is separated, washed with sat. aq. NaHCO$_3$-solution, dried over Na$_2$SO$_4$ and evaporated to give 3-chloro-4,4,4-trifluoro-2-phenyl-but-2-enal (2.20 g) as a pale yellow oil.

b) To a solution of ethyl 2-mercaptoacetate (0.88 g, 6.75 mmol) in THF (45 mL) NaH (271 mg, 6.75 mmol, 60% in mineral oil) is added at −10° C. The mixture is stirred at 0° C. for 30 min before a solution of 3-chloro-4,4,4-trifluoro-2-phenyl-but-2-enal 1.32 g (4.5 mmol) in THF (5 mL) is added. The reaction mixture is stirred at it for 45 min, then treated with 2 N aq. NaOH (2 mL). Stirring is continued for 15 min and the mixture is diluted with water (100 mL) and 1 N aq. NaOH (15 mL). The mixture is extracted with diethyl ether (70 mL). The organic extract is dried over Na$_2$SO$_4$ and evaporated. The crude product is purified by prep. HPLC (Waters Xterra MS18, 75×30 mm, 10 µm, 10 to 95% acetonitrile in water containing 0.5% formic acid) to give 4-phenyl-5-trifluoromethyl-thiophene-2-carboxylic acid ethyl ester (760 mg) as a brownish oil, LC-MS: $t_R$=1.12 min; $^1$H NMR (CDCl$_3$): δ 7.75-7.72 (m, 1H), 7.42 (s, 5H), 4.39 (q, J=7.0 Hz, 2H), 1.40 (t, J=7.0 Hz, 3H).

c) A solution of 4-phenyl-5-trifluoromethyl-thiophene-2-carboxylic acid ethyl ester (750 mg, 2.50 mmol) in ethanol (12 mL) and 2 N aq. LiOH (6 mL) is stirred at 65° C. for 2 h. The reaction mixture is cooled to rt, diluted with water (60 mL) and extracted with DCM (50 mL). The aq. phase is acidified by adding 2 N aq. HCl (7 mL) and extracted twice with DCM (2×50 mL). These organic extracts are combined, washed with sat. aq. NaHCO$_3$, dried over Na$_2$SO$_4$, evaporated and dried under high vacuum to give 4-phenyl-5-trifluoromethyl-thiophene-2-carboxylic acid (670 mg) as a brown solid, LC-MS: t$_R$=0.97 min, $^1$H NMR (D$_6$-DMSO): δ 7.57-7.54 (m, 1H), 7.46-7.42 (m, 5H).

d) To a solution of 4-phenyl-5-trifluoromethyl-thiophene-2-carboxylic acid (272 mg, 1.0 mmol) in THF (10 mL), a solution of MeLi (1.30 mL, 1.6 M solution in diethyl ether) is added. The dark red reaction mixture is stirred at it for 10 min. The reaction is quenched by adding sat. aq. NH$_4$Cl (10 mL). The organic phase is separated, dried over Na$_2$SO$_4$ and evaporated. The crude product is purified by prep. HPLC (Waters Xterra MS18, 75×30 mm, 10 μm, 10 to 95% acetonitrile in water containing 0.5% formic acid) to give 1-(4-phenyl-5-trifluoromethyl-thiophen-2-yl)-ethanone (31 mg) as pale yellow oil, LC-MS: t$_R$=1.06 min, $^1$H NMR (CDCl$_3$): δ 7.62-7.60 (m, 1H), 7.45-7.40 (m, 5H), 2.60 (s, 3H).

d) A solution of 1-(4-phenyl-5-trifluoromethyl-thiophen-2-yl)-ethanone (30 mg, 0.135 mmol) and 3,5-dimethyl-4-hydroxybenzaldehyde (41 mg, 0.27 mmol) in ethanol (1 mL) and 5 N HCl in isopropanol (0.5 mL) is stirred at rt for 18 h. The reaction mixture is diluted with water (10 mL), sat. aq. NaHCO$_3$ (15 mL) and 1 N NaOH, and extracted with DCM (25 mL). The organic extract is dried over Na$_2$SO$_4$ and evaporated to give 3-(4-hydroxy-3,5-dimethyl-phenyl)-1-(4-phenyl-5-trifluoromethyl-thiophen-2-yl)-propenone (38 mg) as a brown solid, LC-MS: t$_R$=1.17 min.

e) A solution of 3-(4-hydroxy-3,5-dimethyl-phenyl)-1-(4-phenyl-5-trifluoromethyl-thiophen-2-yl)-propenone (30 mg, 0.075 mmol) in ethanol (3 mL) is treated with Pd/C (25 mg, 10% Pd) and the resulting suspension is stirred at it for 1 h under 1 atm H$_2$. The mixture is filtered over celite and the solvent is removed in vacuo to give 3-(4-hydroxy-3,5-dimethyl-phenyl)-1-(4-phenyl-5-trifluoromethyl-thiophen-2-yl)-propan-1-one (28 mg) as a green oil, LC-MS: t$_R$=1.13 min, $^1$H NMR (CDCl$_3$): δ 7.56-7.53 (m, 1H), 7.46-7.38 (m, 5H), 6.83 (s, 2H), 4.48 (s, 1H), 3.18 (t, J=7.6 Hz, 2H), 2.94 (t, J=7.6 Hz, 2H), 2.21 (s, 6H).

Example 2

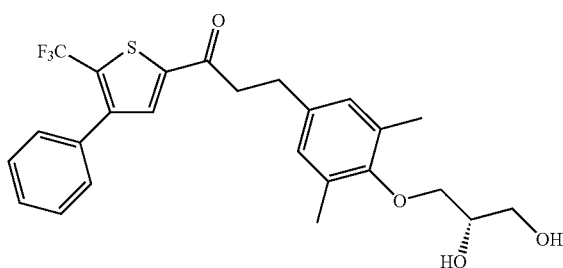

A solution of 3-(4-hydroxy-3,5-dimethyl-phenyl)-1-(4-phenyl-5-trifluoromethyl-thiophen-2-yl)-propan-1-one (8 mg, 20 μmol) in 2-propanol (0.7 mL) and 2 N aq. NaOH (0.27 mL) is treated with (S)-3-chloro-propane-1,2-diol (9 mg, 80 μmol) and the mixture is stirred at 65° C. for 24 h. The mixture is cooled to rt, diluted with formic acid (0.25 mL) and separated by prep. HPLC (Waters Xterra MS18 19×50 mm 5 μm, 10 to 95% acetonitrile in water containing 0.5% formic acid) to give 3-[4-((S)-2,3-dihydroxy-propoxy)-3,5-dimethyl-phenyl]-1-(4-phenyl-5-trifluoro-methyl-thiophen-2-yl)-propan-1-one (3 mg) as a colourless lyophilisate; LC-MS: t$_R$=1.06 min, [M+1]$^+$=479.21.

Example 3

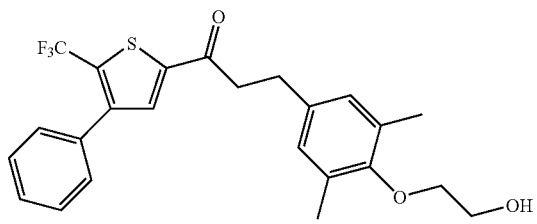

A solution of 3-(4-hydroxy-3,5-dimethyl-phenyl)-1-(4-phenyl-5-trifluoromethyl-thiophen-2-yl)-propan-1-one (8 mg, 20 μmol) in 2-propanol (0.7 mL) and 2 N aq. NaOH (0.27 mL) is treated with 2-bromoethanol (10 mg, 80 μmol) and the mixture is stirred at 65° C. for 2 h. The mixture is cooled to rt, diluted with formic acid (0.25 mL) and separated by prep. HPLC (Waters Xterra MS18 19×50 mm 5 μm, 10 to 95% acetonitrile in water containing 0.5% formic acid) to give 3-[4-(2-hydroxy-ethoxy)-3,5-dimethyl-phenyl]-1-(4-phenyl-5-trifluoro-methyl-thiophen-2-yl)-propan-1-one (4 mg) as a colourless lyophilisate; LC-MS: t$_R$=1.12 min, [M+1]$^+$=449.15.

Example 4

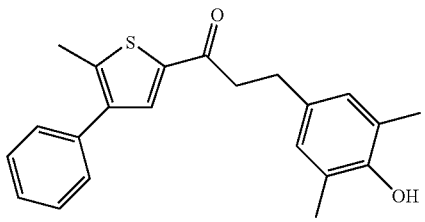

a) Phosphoroxy chloride (17 mL, 186 mmol) is slowly added to DMF (17 mL) at 5° C. and the mixture is stirred at rt for 40 min before phenylacetone (9.5 mL, 74.5 mmol) is added at 8° C. The reaction mixture is stirred for 1 h at 8° C., then at 72° C. for 3.5 h. The mixture is cooled to rt, diluted with water/ice and buffered by adding Na-acetate (40 g). The solution is extracted twice with EA (250 mL). The organic extracts are washed with water and evaporated. The crude product is purified by CC on silica gel eluting with heptane:EA 4:1 to give 3-chloro-2-phenyl-but-2-enal (8.96 g) as an orange liquid; $^1$H NMR (CDCl$_3$): δ 10.42 (s, 1H), 7.42-7.30 (m, 5H), 2.29 (s, 3H).

b) Ethyl 2-mercaptoacetate (5.92 g, 49.3 mmol) is added to a freshly prepared solution of sodium (1.2 g, 50 mmol) in ethanol (50 mL). To this solution 3-chloro-2-phenyl-but-2-enal (8.90 g, 49.3 mmol) is added and the mixture is stirred at rt for 16 h, then at 70° C. for 2 h. A 2 N aq. solution of LiOH (30 mL) is added and stirring is continued at 70° C. for 2 h. The ethanol is removed in vacuo, the remaining mixture is diluted with water and extracted with DCM. The aq. phase is acidified with aq. HCl and extracted with diethyl ether. The solvent of the ether phase is evaporated, the residue is suspended in acetonitrile, filtered and washed with additional acetonitrile and dried to give 5-methyl-4-phenyl-thiophene-2-carboxylic acid (4.45 g) as a yellow powder, LC-MS: $t_R$=0.92 min, [M+1+MeCN]$^+$=260.13; $^1$H NMR (CDCl$_3$): δ 7.84 (s, 1H), 7.46-7.33 (m, 5H), 2.55 (s, 3H).

c) To a solution of 5-methyl-4-phenyl-thiophene-2-carboxylic acid (1.50 g, 6.87 mmol) in diethyl ether (100 mL) MeLi (7 mL, 1.5 M in diethyl ether) is added at 5° C. The mixture is stirred at it for 90 min before another portion of MeLi (1 mL) is added. Stirring is continued for 1 h. The mixture is diluted with water and extracted with EA. The organic extracts are evaporated and the crude product is purified by CC on silica gel eluting with heptane:EA 4:1 to give 1-(5-methyl-4-phenyl-thiophen-2-yl)-ethanone (490 mg) as a colourless oil, LC-MS: $t_R$=1.00 min, [M+1]$^+$=217.10; $^1$H NMR (CDCl$_3$): δ 7.62 (s, 1H), 7.48-7.33 (m, 5H), 2.54 (s, 6H).

d) A solution of 1-(5-methyl-4-phenyl-thiophen-2-yl)-ethanone (419 mg, 1.94 mmol) and 3,5-dimethyl-4-hydroxy-benzaldehyde (350 mg, 2.33 mmol) in ethanol (4 mL) and 5 N HCl in isopropanol (2 mL) is stirred at it for 1 h. The dark green solution is diluted with water and extracted with EA. The organic extract is evaporated, dissolved in ethanol (10 mL) and treated with Pd/C (60 mg, 10% Pd). The slurry is hydrogenated under 1.4 bar of H$_2$ for 6 h. The mixture is filtered, the solvent is removed in vacuo and the crude product is purified by CC on silica gel eluting with heptane:EA 4:1 to give 3-(4-hydroxy-3,5-dimethyl-phenyl)-1-(5-methyl-4-phenyl-thiopen-2-yl)-propan-1-one (360 mg) as a colourless resin; LC-MS: $t_R$=1.09 min, [M+1]$^+$=351.25; $^1$H NMR (CDCl$_3$): δ 7.60 (s, 1H), 7.46-7.30 (m, 5H), 6.85 8s, 2H), 4.48 (s, 1H), 3.14 (dd, J=7.0, 8.2 Hz, 2H), 2.92 (dd, J=7.0, 8.2 Hz, 2H), 2.52 (s, 3H), 2.21 (s, 6H).

Example 5

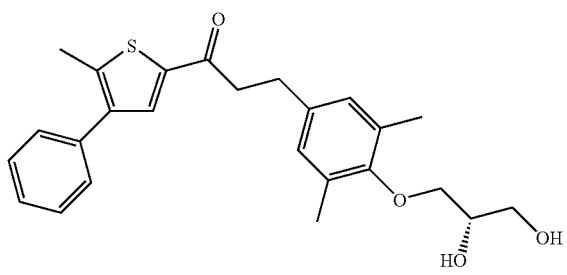

A solution of 3-(4-hydroxy-3,5-dimethyl-phenyl)-1-(5-methyl-4-phenyl-thiophen-2-yl)-10 propan-1-one (60 mg, 0.172 mmol) in 2-propanol (1 mL) and 3 N aq. NaOH (0.3 mL) is treated with (S)-3-chloro-propane-1,2-diol (95 mg, 0.86 mmol) and the mixture is stirred at 70° C. for 24 h. The solvent is evaporated and the residue is purified on prep. TLC plates with EA to give 3-[4-((S)-2,3-dihydroxy-propoxy)-3,5-dimethyl-phenyl]-1-(5-methyl-4-phenyl-thiophen-2-yl)-propan-1-one (44 mg) as an oil; LC-MS: $t_R$=1.00 min, [M+1]$^+$=425.23; $^1$H NMR (CDCl$_3$): δ 7.60 (s, 1H), 7.46-7.32 (m, 5H), 6.88 (s, 2H), 4.11-4.06 (m, 1H), 3.86-3.80 (m, 4H), 3.19-3.11 (m, 2H), 2.98-2.91 (m, 2H), 2.72 (d, J=5.3 Hz, 1H), 2.53 (s, 3H), 2.25 (s, 6H), 2.11-2.05 (m, 1H).

Example 6

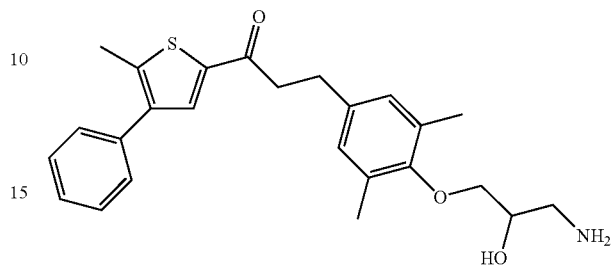

a) A solution of 3-(4-hydroxy-3,5-dimethyl-phenyl)-1-(5-methyl-4-phenyl-thiophen-2-yl)-propan-1-one (300 mg, 0.86 mmol) in 2-propanol (7.5 mL) and 3 N aq. NaOH (2.5 mL) is treated with epichlorohydrine (158 mg, 1.72 mmol) and the mixture is stirred at rt for 24 h, then diluted with water and extracted with EA. The solvent of the organic extract is evaporated and the residue is purified by CC on silica gel eluting with hepaten:EA 5:1 to give 3-(3,5-dimethyl-4-oxiranylmethoxy-phenyl)-1-(5-methyl-4-phenyl-thiophen-2-yl)-propan-1-one (92 mg) as an oil; LC-MS: $t_R$=1.13 min, [M+1]$^+$=407.24.

b) A solution of 3-(3,5-dimethyl-4-oxiranylmethoxy-phenyl)-1-(5-methyl-4-phenyl-thiophen-2-yl)-propan-1-one (30 mg, 74 µmol) in methanol (1 mL) and ammonia (22 µL, approx. 7 N solution in methanol) is stirred at 65° C. for 4 h and at rt for 18 h. The solvent is removed in vacuo and the residue is purified by prep. HPLC to give 3-[4-(3-amino-2-hydroxy-propoxy)-3,5-dimethyl-phenyl]-1-(5-methyl-4-phenyl-thiophen-2-yl)-propan-1-one (4 mg) as a colourless resin; LC-MS: $t_R$=0.87 min, [M+1]$^+$=424.24.

Example 7

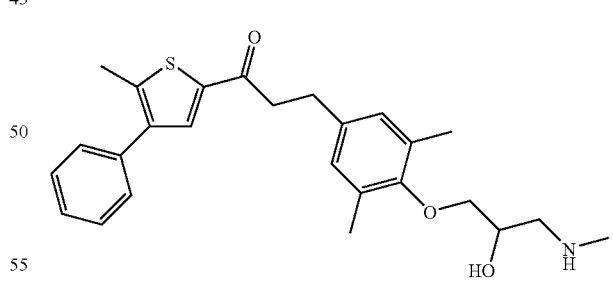

A solution of 3-(3,5-dimethyl-4-oxiranylmethoxy-phenyl)-1-(5-methyl-4-phenyl-thiophen-2-yl)-propan-1-one (33 mg, 82 µmol) and methylamine (0.082 mL, 2 M solution in THF) in methanol (1 mL) is stirred at 65° C. for 4 h and at rt for 18 h. The solvent is removed in vacuo and the residue is purified by prep. HPLC to give 3-[4-(2-hydroxy-3-methylamino-propoxy)-3,5-dimethyl-phenyl]-1-(5-methyl-4-phenyl-thiophen-2-yl)-propan-1-one (4 mg) as a colourless resin; LC-MS: $t_R$=0.88 min, [M+1]$^+$=438.25, $^1$H NMR (as formate salt) (CDCl$_3$): δ 8.56 (s, 1H), 7.60 (s, 1H), 7.45-7.30 (m, 5H), 6.85 (m, 2H), 4.60 (s br, 2H), 4.37-4.30 (m, 1H), 3.81-3.20 (m, 2H), 3.18-3.10 (m, 4H), 2.96-2.88 (m, 2H), 2.70 (s, 3H), 2.51 (s, 3H), 2.20 (s, 6H).

Example 8

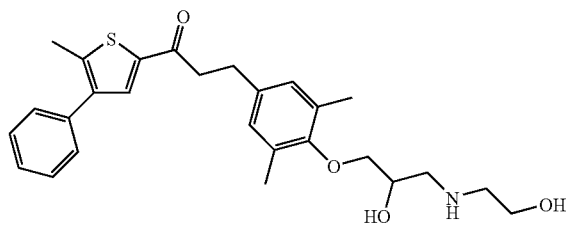

A solution of 3-(3,5-dimethyl-4-oxiranylmethoxy-phenyl)-1-(5-methyl-4-phenyl-thiophen-2-yl)-propan-1-one (30 mg, 74 μmol) and aminoethanol (9 mg, 0.148 mmol) in methanol (1 mL) is stirred at 65° C. for 4 h. The solvent is removed in vacuo and the residue is purified by prep. HPLC to give 3-{4-[2-hydroxy-3-(2-hydroxy-ethylamino)-propoxy]-3,5-dimethyl-phenyl}-1-(5-methyl-4-phenyl-thiophen-2-yl)-propan-1-one (22 mg) as a colourless resin; LC-MS: $t_R$=0.88 min, [M+1]$^+$=468.28.

Example 9

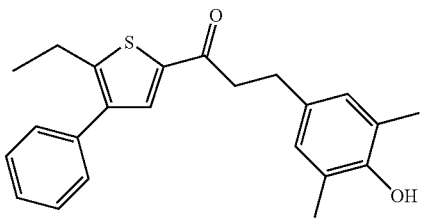

a) At −78° C., a solution of 4-phenylthiophene-2-carboxylic acid (800 mg, 3.92 mmol) in THF (10 mL) is treated with tert.-BuLi (8 mL, 1.6 M in pentane). The mixture is stirred at −70° C. for 40 min before iodomethane (1 mL) is added. Stirring is continued for 5 h at −78° C., then the reaction mixture is allowed to warm to rt overnight. The reaction is quenched with sat. aq. NH$_4$Cl and extracted with EA. The organic extract is dried over MgSO$_4$, the solvent is removed and the crude product is purified by CC on silica gel eluting with DCM containing 3% of methanol to give 5-ethyl-4-phenyl-thiophene-2-carboxylic acid (340 mg) as a red solid; LC-MS: $t_R$=0.95 min, [M+1+MeCN]$^+$=274.15; $^1$H NMR (CDCl$_3$): δ 7.79 (s, 1H), 7.46-7.31 (m, 5), 2.92 (q, J=7.6 Hz, 2H), 1.30 (t, J=7.6 Hz, 3H).

b) At 5° C. a solution of 5-ethyl-4-phenyl-thiophene-2-carboxylic acid (180 mg, 0.775 mmol) in THF (4 mL) is treated with MeLi (0.9 mL, 1.6 M in diethyl ether). The reaction mixture is stirred at rt for 30 min before another portion of MeLi (0.5 mL) is added. Stirring is continued for 1 h, the reaction is quenched by adding water (50 mL) and extracted with EA. The organic extract is dried over MgSO$_4$, the solvent is removed in vacuo, and the crude product is purified by CC on silica gel eluting with heptane:EA 30:1 to give 1-(5-ethyl-4-phenyl-thiophen-2-yl)-ethanone (64 mg) as a colourless oil; LC-MS: $t_R$=1.03 min, [M+1+MeCN]$^+$=272.15; $^1$H NMR (CDCl$_3$): δ 7.60 (s, 1H), 7.47-7.32 (m, 5H), 2.91 (q, J=7.6 Hz, 2H), 2.54 (s, 3H), 1.30 (t, J=7.6 Hz, 3H).

c) A solution of 1-(5-ethyl-4-phenyl-thiophen-2-yl)-ethanone (64 mg, 0.278 mmol) and 3,5-dimethyl-4-hydroxybenzaldehyde (53 mg, 0.334 mmol) in ethanol (1.2 mL) and 5 N HCl in isopropanol (0.6 mL) is stirred at rt for 1 h. The dark green solution is diluted with water and extracted with EA. The organic extract is evaporated, dissolved in methanol (1 mL) and THF (1 mL), and treated with Pd/C (60 mg, 10% Pd). The slurry is hydrogenated under 1.4 bar of H$_2$ for 1.5 h. The mixture is filtered over celite, the solvent is removed in vacuo and the crude product is purified on prep. TLC plates with heptane:EA 2:1 to give 3-(4-hydroxy-3,5-dimethyl-phenyl)-1-(5-ethyl-4-phenyl-thiophen-2-yl)-propan-1-one (59 mg) as a yellow oil; LC-MS: $t_R$=1.11 min; $^1$H NMR (CDCl$_3$): δ 7.58 (s, 1H), 7.46-7.30 (m, 5H), 6.85 (s, 2H), 4.56 (s, 1H), 3.18-3.10 (m, 2H), 2.97-2.86 (m, 4H), 2.22 (s, 6H), 1.30 (t, J=7.6 Hz, 3H).

Example 10

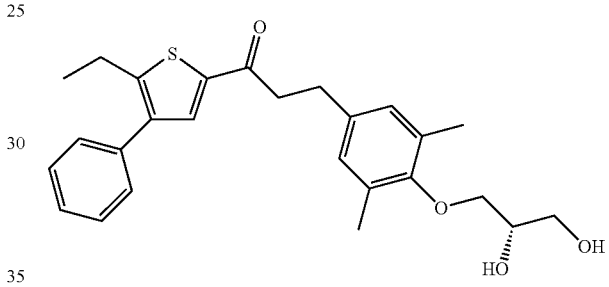

A solution of 3-(4-hydroxy-3,5-dimethyl-phenyl)-1-(5-ethyl-4-phenyl-thiophen-2-yl)-propan-1-one (52 mg, 0.143 mmol) in 2-propanol (1 mL) and 3 N aq. NaOH (0.3 mL) is treated with (S)-3-chloro-propane-1,2-diol (79 mg, 0.71 mmol) and the mixture is stirred at 70° C. for 15 h. The reaction mixture is diluted with water and extracted with DCM. The solvent of the organic extract is evaporated and the crude product is purified on prep. TLC plates with heptane: EA 1:3 to give 3-[4-((S)-2,3-dihydroxy-propoxy)-3,5-dimethyl-phenyl]-1-(5-ethyl-4-phenyl-thiophen-2-yl)-propan-1-one (14 mg) as a colourless resin; LC-MS: $t_R$=1.03 min, [M+1]$^+$=439.25; $^1$H NMR (CDCl$_3$): δ 7.58 (s, 1H), 7.45-7.30 (m, 5H), 6.88 (s, 2H), 4.11-4.04 (m, 1H), 3.87-3.80 (m, 4H), 3.67-3.60 (m, 2H), 3.60-3.56 (m, 1H), 3.48-3.40 (m, 1H), 3.20-3.10 (m, 2H), 2.98-2.87 (m, 4H), 2.25 (s, 6H), 1.30 (t, J=7.6 Hz, 3H).

Example 11

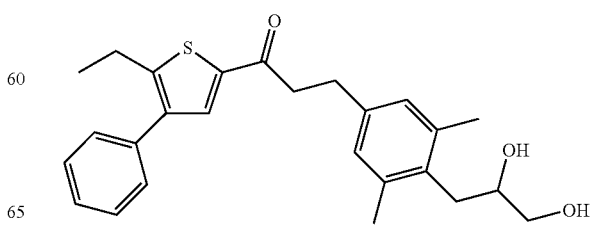

a) To a cold solution (5° C.) of 3,5-dimethyl-4-hydroxy-benzaldehyde (2.5 g, 16.6 mmol) in DCM (25 mL) and pyridine (3.8 mL), trifluoromethanesulfonic acid anhydride (3 mL) is slowly added. Upon complete addition, the mixture is warmed to rt and stirred for 2 h. The mixture is diluted with EA (150 mL) and washed with water (2×100 mL) The solvent of the organic phase is evaporated and the crude product is purified by CC on silica gel eluting with heptane:EA 3:1 to give trifluoro-methanesulfonic acid 4-formyl-2,6-dimethyl-phenyl ester (3.13 g) as a colourless liquid.

b) To a solution of trifluoromethanesulfonic acid 4-formyl-2,6-dimethyl-phenyl ester (3.13 g, 11.1 mmol), bis(triphenylphosphine)palladium dichloride (682 mg, 0.972 mmol), triphenylphosphine (1.76 g, 6.7 mmol), LiCl (3.98 g, 93.8 mmol) and a trace of 2,6-di-tert.-butyl-4-methylphenol in DMF (30 mL), allyltributylstannane (2 mL) is added. The mixture is heated to 120° C. and stirred for 2 h before another portion of allyltributylstannane (2 mL) is added. Stirring is continued at 120° C. for 1 h. The mixture is cooled to rt, diluted with water (100 mL) and extracted with EA. The organic extract is washed with 1.5 M aq. HCl (2×100 mL), dried over MgSO$_4$, and the solvent is evaporated. The crude product is purified by CC on silica gel eluting with heptane:EA 20:1 to give 4-allyl-3,5-dimethyl-benzaldehyde (1.34 g) as a colourless liquid; $^1$H NMR (CDCl$_3$: δ 9.92 (s, 1H), 7.53 (s, 2H), 5.96-5.80 (m, 1H), 5.06-5.00 (m, 1H), 4.87-4.78 (m, 1H), 3.48-3.40 (m, 2H), 2.38 (s, 6H).

c) To a solution of 4-allyl-3,5-dimethyl-benzaldehyde (500 mg, 2.87 mmol) in acetone (10 mL) and water (0.4 mL), N-methylmorpholine-N-oxide (465 mg, 3.44 mmol) and OsO$_4$ (1 mL, 2.5% solution in tert.-butanol) is added. The reaction mixture is stirred at rt for 3 h before it is diluted with DCM and washed with 10% aq.

citric acid solution. The organic layer is dried over MgSO$_4$ and the solvent is removed in vacuo. The crude product is purified by CC on silica gel eluting with EA to give 4-(2,3-dihydroxy-propyl)-3,5-dimethyl-benzaldehyde (190 mg) as a colourless oil; LC-MS: $t_R$=0.69 min, [M+1+CH$_3$CN]$^+$= 250.28.

d) A solution of 4-(2,3-dihydroxy-propyl)-3,5-dimethyl-benzaldehyde (64 mg, 0.308 mmol) and 1-(5-ethyl-4-phenyl-thiophen-2-yl)-ethanone (50 mg, 0.218 mmol) in ethanol (2 mL) and 5 N HCl in isopropanol (0.5 mL) is stirred at rt for 5 days. The solvent is removed in vacuo and the residue is separated by prep. HPLC. Product containing fractions are treated with sat. aq. NaHCO$_3$ and 3 M aq. NaOH (5 mL). The mixture is stirred at rt for 1 h, then extracted with DCM. The solvent of the organic extract is removed. The residue is dissolved in THF:methanol 1:1 (5 mL) and is treated with Pd/C. The slurry is stirred at it for 16 h under 1.5 bar of H$_2$. The mixture is filtered over celite and the filtrate is evaporated to give 3-[4-(2,3-dihydroxy-propyl)-3,5-dimethyl-phenyl]-1-(5-ethyl-4-phenyl-thiophen-2-yl)-propan-1-one (20 mg) as a colourless oil, LC-MS: $t_R$=1.04 min, [M+1]$^+$=423.28.

Example 12 a) A solution of 3-(4-hydroxy-3,5-dimethyl-phenyl)-1-(5-ethyl-4-phenyl-thiophen-2-yl)-propan-1-one (296 mg, 0.81 mmol) in 2-propanol (2.5 mL) and 3 N aq. NaOH (1 mL) is treated with epichlorohydrine (150 mg, 1.63 mmol) and the mixture is stirred at it for 24 h, then diluted with water and extracted with EA. The solvent of the organic extract is evaporated and the residue is purified by CC on silica gel eluting with hepaten:EA 4:1 to give 3-(3,5-dimethyl-4-oxiranyl-methoxy-phenyl)-1-(5-ethyl-4-phenyl-thiophen-2-yl)-propan-1-one (160 mg) as a pale yellow oil; LC-MS: $t_R$=1.16 min, [M+1]$^+$=421.22, $^1$H NMR (CDCl$_3$): δ 7.58 (s, 1H), 7.45-7.30 (m, 5H), 6.88 (m, 2H), 3.99 (dd, J=2.9, 11.1 Hz, 1H), 3.72 (dd, J=5.8, 11.1 Hz, 1H), 3.38-3.31 (m, 1H), 3.19-3.11 (m, 2H), 2.98-2.85 (m, 5H), 2.72-2.67 (m, 1H), 2.26 (s, 6H), 1.30 (t, J=7.6 Hz, 3H).

b) A solution of 3-(3,5-dimethyl-4-oxiranylmethoxy-phenyl)-1-(5-ethyl-4-phenyl-thiophen-2-yl)-propan-1-one (30 mg, 72 μmol) in methanol (2 mL) and ammonia (22μL, 7 N solution in methanol) is stirred for 16 h at it and for 16 h at 40° C. before the solvent is evaporated. The residue is separated by prep. HPLC to give the formate salt of 3-[4-(3-amino-2-hydroxy-propoxy)-3,5-dimethyl-phenyl]-1-(5-ethyl-4-phenyl-thiophen-2-yl)-propan-1-one (4 mg) as a colourless resin; LC-MS: $t_R$=0.89 min, [M+1]$^+$=438.24, $^1$H NMR (CDCl$_3$): δ 8.54 (s, 1H), 7.56 (s, 1H), 7.42-7.26 (m, 5H), 6.79 (s, 2H), 5.22 (s br, 3H), 4.26-4.18 (m, 1H), 3.75-3.66 (m, 2H), 3.24-3.06 (m, 3H), 2.94-2.80 (m, 4H), 2.28-2.20 (m, 1H), 2.14 (s, 6H), 1.28 (t, J=7.0 Hz, 3H).

Example 13

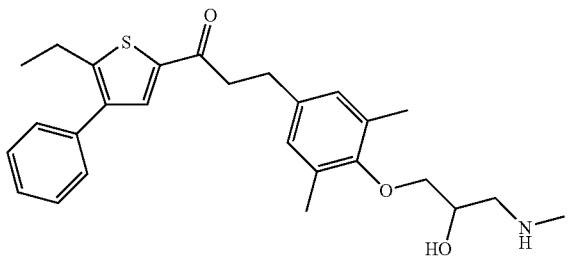

A solution of 3-(3,5-dimethyl-4-oxiranylmethoxy-phenyl)-1-(5-ethyl-4-phenyl-thiophen-2-yl)-propan-1-one (30 mg, 72 μmol) and methylamine (80 μL, 2 M solution in THF) in methanol (2 mL) is stirred for 16 h at it and for 16 h at 40° C. before the solvent is evaporated. The residue is separated by prep. HPLC to give the formate salt of 1-(5-ethyl-4-phenyl-thiophen-2-yl)-3-[4-(2-hydroxy-3-methylamino-propoxy)-3,5-dimethyl-pheny1]-propan-1-one (4 mg) as a colourless resin; LC-MS: $t_R$=0.91 min, [M+1]$^+$=452.25.

Example 14

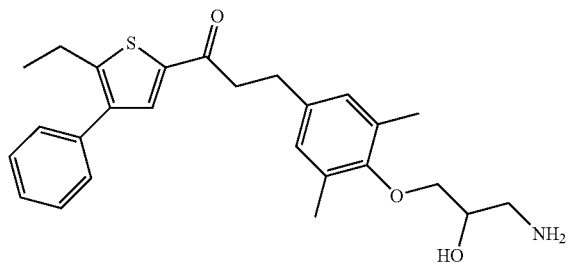

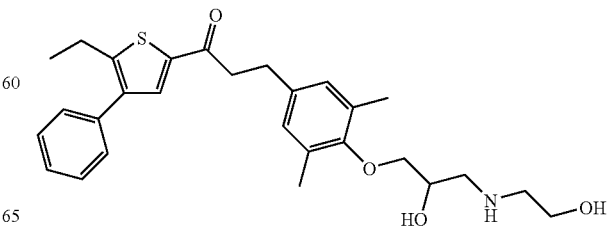

A solution of 3-(3,5-dimethyl-4-oxiranylmethoxy-phenyl)-1-(5-ethyl-4-phenyl-thiophen-2-yl)-propan-1-one (30 mg, 72 μmol) and aminoethanol (9 mg, 150 μmol) in methanol (2 mL) is stirred for 4 h at 60° C. before the solvent is evaporated. The residue is separated by prep. HPLC to give the formate salt of 1-(5-ethyl-4-phenyl-thiophen-2-yl)-3-{4-[2-hydroxy-3-(2-hydroxy-ethylamino)-propoxy]-3,5-dimethyl-phenyl}-propan-1-one (14 mg) as a colourless resin; LC-MS: $t_R$=0.89 min, $[M+1]^+$=482.32, $^1$H NMR (CDCl$_3$): δ 8.54 (s, 1H), 7.57 (s, 1H), 7.45-7.30 (m, 5H), 6.85 (s, 2H), 4.34-4.26 (m, 1H), 3.88-3.84 (m, 2H), 3.80-3.75 (m, 2H), 3.65 (s br, 4H), 3.23-3.05 (m, 6H), 2.98-2.86 (m, 4H), 2.21 (s, 6H), 1.29 (t, J=7.6 Hz, 3H).

Example 15

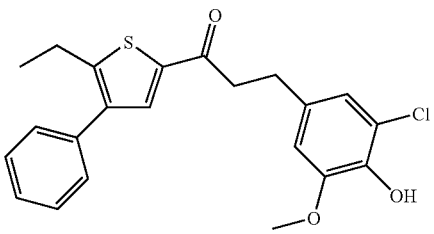

A solution of 1-(5-ethyl-4-phenyl-thiophen-2-yl)-ethanone (200 mg, 0.869 mmol) and 3-chloro-4-hydroxy-5-methoxybenzaldehyde (194 mg, 1.04 mmol) in ethanol (2 mL) and 5 N HCl in isopropanol (1 mL) is stirred at rt for 18 h. The dark green solution is diluted with water and extracted with EA. The organic extract is evaporated, dissolved in methanol (5 mL) and THF (5 mL) and treated with Pd/C (150 mg, 10% Pd). The slurry is hydrogenated under 1.8 bar of H$_2$ for 18 h. The mixture is filtered over celite, the solvent is removed in vacuo and the crude product is purified by CC on silica gel eluting with heptane:EA 7:3 to give 3-(3-chloro-4-hydroxy-5-methoxy-phenyl)-1-(5-ethyl-4-phenyl-thiophen-2-yl)-propan-1-one (208 mg) as a colourless oil; LC-MS: $t_R$=1.10 min, $[M+1]^+$=401.12; $^1$H NMR (CDCl$_3$): δ 7.58 (s, 1H), 7.46-7.30 (m, 5H), 6.83 (d, J=1.8 Hz, 1H), 6.67 (d, J=1.8 Hz, 1H), 3.88 (s, 3H), 3.16 (t, J=7.6 Hz, 2H), 2.98 (t, J=7.6 Hz, 2H), 2.91 (q, J=7.6 Hz, 2H), 1.30 (t, J=7.6 Hz, 3H).

Example 16

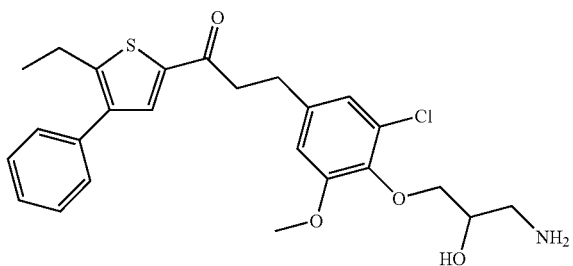

a) A solution of 3-(3-chloro-4-hydroxy-5-methoxy-phenyl)-1-(5-ethyl-4-phenyl-thiophen-2-yl)-propan-1-one (150 mg, 0.375 mmol) in 2-propanol (3 mL) and 3 N aq. NaOH (1 mL) is treated with epichlorohydrine (104 mg, 1.12 mmol) and the mixture is stirred at 70° C. for 24 h, then diluted with water and extracted with EA. The solvent of the organic extract is evaporated and the residue is purified by CC on silica gel eluting with heptane:EA 1:1 to give 3-(3-chloro-4-hydroxy-5-methoxy-phenyl)-1-(5-ethyl-4-phenyl-thiophen-2-yl)-propan-1-one (100 mg) a colourless oil; LC-MS: $t_R$=1.14 min, $[M+1]^+$=457.13.

b) A solution of 3-(3-chloro-4-hydroxy-5-methoxy-phenyl)-1-(5-ethyl-4-phenyl-thiophen-2-yl)-propan-1-one (50 mg, 110 μmol) in methanol (2 mL) and ammonia (53 μL, 7 N solution in methanol) is stirred for 16 h at 60° C. before the solvent is evaporated. The residue is separated by prep. HPLC to give the formate salt of 3-[4-(3-amino-2-hydroxy-propoxy)-3,5-dimethyl-phenyl]-1-(5-ethyl-4-phenyl-thiophen-2-yl)-propan-1-one (5 mg) as a colourless resin; LC-MS: $t_R$=0.90 min, $[M-1]^+$=474.28.

Example 17

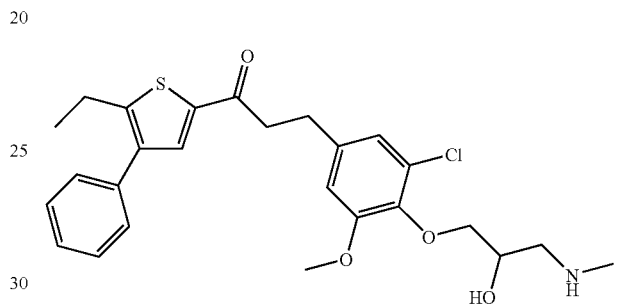

A solution of 3-(3-chloro-4-hydroxy-5-methoxy-phenyl)-1-(5-ethyl-4-phenyl-thiophen-2-yl)-propan-1-one (50 mg, 110 μmol) and methylamine (55 μL, 2 M solution in THF) in methanol (4 mL) is stirred for 16 h at rt and for 16 h at 70° C. before the solvent is evaporated. The residue is separated by prep. HPLC to give the formate salt of 3-[3-chloro-4-(2-hydroxy-3-methylamino-propoxy)-5-methoxy-phenyl]-1-(5-ethyl-4-phenyl-thiophen-2-yl)-propan-1-one (7 mg) as a colourless oil; LC-MS: $t_R$=0.90 min, $[M+1]^+$=488.18.

Example 18

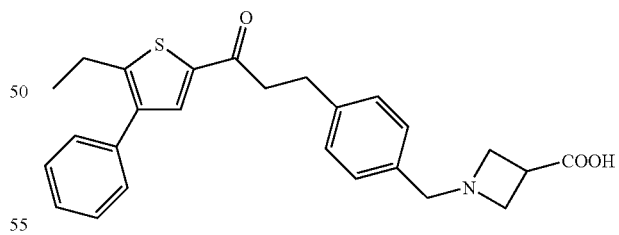

a) A solution of 1-(5-ethyl-4-phenyl-thiophen-2-yl)-ethanone (600 mg, 2.61 mmol) and terephthalaldehyde (874 mg, 6.51 mmol) in ethanol (10 mL) and 5 N HCl in isopropanol (5 mL) is stirred at rt for 3 days. The reaction mixture is diluted with water and extracted with diethyl ether. The organic extract is washed with water and sat. aq. NaHCO$_3$ solution and the solvent is evaporated. The crude product is purified by CC on silica gel eluting with heptane:EA 4:1 to give 4-[3-(5-ethyl-4-phenyl-thiophen-2-yl)-3-oxo-propenyl]-benzaldehyde (280 mg) as a yellow solid, LC-MS: $t_R$=1.14 min, $[M+1]^+$=347.14, $^1$H NMR (CDCl$_3$): δ 10.05 (s, 1H), 7.95-

7.88 (m, 2H), 7.84-7.77 (m, 3H), 7.52-7.35 (m, 5H), 2.96 (q, J=7.6 Hz, 2H), 1.35 (t, J=7.6 Hz, 3H).

b) A solution of 4-[(5-ethyl-4-phenyl-thiophen-2-yl)-3-oxo-propenyl]-benzaldehyde (140 mg, 0.405 mmol) and azetidine-3-carboxylic acid (51 mg, 0.506 mmol) and NaBH(OAc)$_3$ (257 mg, 1.21 mmol) in THF (6 mL) is stirred at rt for 6 h. The reaction mixture is diluted with a small amount of methanol and DCM (150 mL) and washed with water. The organic phase is separated and the aqueous phase again extracted with DCM. The combined organic extracts are dried over MgSO$_4$ and evaporated. The residue is suspended in methanol, filtered and dried. The solid material obtained is suspended in DMF/methanol and treated with Pd/C (20 mg, 10% Pd). The slurry is stirred under 1.5 bar of H$_2$ at rt for 16 h. The mixture is filtered and the filtrate is evaporated and dried to give 1-{4-[3(5-ethyl-4-phenyl-thiophen-2-yl)-3-oxo-propyl]benzyl}azetidine-3-carboxylic acid (15 mg) as a colourless solid; LC-MS: $t_R$=0.89 min, [M+1]$^+$=434.17.

Example 19

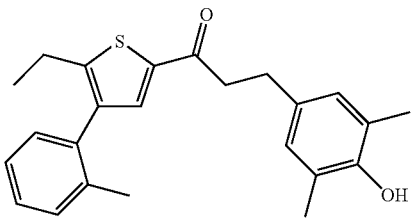

a) At 5° C., o-tolyl-acetaldehyde (3.50 g, 29 mmol) is added to a mixture of POCl$_3$ (7.5 mL, 93 mmol) and DMF (8 mL). The mixture is stirred at 70° C. for 3 h before the reaction is quenched by adding water/ice and NaOAc (17 g) and extracted with EA (2×150 mL). The solvent of the organic extract is evaporated and the product is purified by CC on silica gel eluting with heptane:EA 9:1. The resulting oil (2.5 g) is dissolved in ethanol (5 mL) and then added dropwise to a freshly prepared solution of Na (318 mg, 13.8 mmol) and ethyl-2-mercaptoacetate (1.64 g, 13.6 mmol) in ethanol (15 mL). The reaction mixture is stirred at rt for 16 h, then at 70° C. for 2 h. 3 M aq. NaOH (15 mL) is added and the mixture is stirred at 70° C. for 2 h. The mixture is cooled to rt, diluted with water and extracted with DCM. The aqueous phase is acidified with aq. HCl and extracted with EA. The organic extract is dried over MgSO$_4$ and the solvent is evaporated to give crude 4-o-tolyl-thiophene-2-carboxylic acid (790 mg) as a brown solid; LC-MS: $t_R$=0.91 min.

b) At −70° C. a solution of 4-o-tolyl-thiophene-2-carboxylic acid (790 mg, 3.62 mmol) in THF (10 mL) is treated with tert.-BuLi (6.5 mL, 1.7 M solution in pentane). The mixture is stirred at −70° C. for 30 min before ethyliodide (1.5 mL) is added. The mixture is warmed to rt and stirring is continued for 16 h. The reaction is quenched by adding sat. aq. NH$_4$Cl and the mixture is extracted with EA. The solvent of the organic extracts is evaporated and the remaining oil (680 mg) is dissolved in dry DCM (10 mL). TBTU (1.24 g, 3.87 mmol), N,O-dimethylhydroxylamine (415 mg, 4.25 mmol) and DIPEA (2 mL) is added and the mixture is stirred at it for 20 h before it is diluted with EA and washed with water. The organic layer is separated, evaporated and the remaining residue is purified by CC on silica gel eluting with heptane:EA 9:1 to 2:1 to give 5-ethyl-4-o-tolyl-thiophene-2-carboxylic acid methoxy-methyl-amide (58 mg) as an oil. This oil is dissolved in THF (4 mL) and treated at 4° C. with methyl magnesiumbromide (0.1 mL, 3 M solution in THF). The reaction mixture is stirred at it for 16 h before another portion of the Grignard reagent (0.2 mL) is added. Stirring is continued for 72 h. The mixture is diluted with water and extracted with EA (50 mL). The solvent of the organic extract is evaporated to give crude 1-(5-ethyl-4-o-tolyl-thiophen-2-yl)-ethanone (58 mg) as a yellow oil; LC-MS: $t_R$=1.05 min, [M+1]$^+$=245.16.

c) A solution of 1-(5-ethyl-4-o-tolyl-thiophen-2-yl)-ethanone (51 mg, 0.209 mmol) and 3,5-dimethyl-4-hydroxybenzaldehyde (47 mg, 0.172 mmol) in ethanol (1.5 mL) and 5 N HCl in isopropanol (0.7 mL) is stirred at it for 18 h. The solution is diluted with water and extracted with EA. The organic extract is evaporated, dissolved in methanol (3 mL) and THF (3 mL) and treated with Pd/C (10 mg, 10% Pd). The slurry is stirred under 1.5 bar of H$_2$ for 18 h. The mixture is filtered, the solvent of the filtrate is removed in vacuo and the crude product is purified on prep. TLC plates with heptane:EA 3:1 to give 1-(5-ethyl-4-o-tolyl-thiophen-2-yl)-3-(4-hydroxy-3,5-dimethyl-phenyl)-propan-1-one (18 mg) as a colourless oil; LC-MS: $t_R$=1.12 min, [M+1]$^+$=379.24.

Example 20

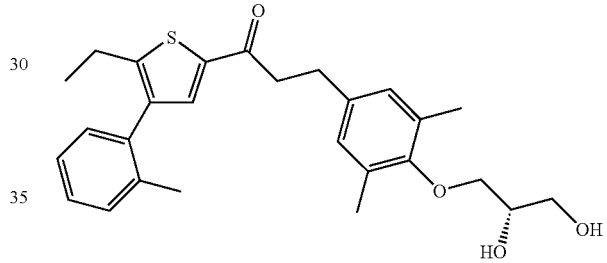

A solution of 1-(5-ethyl-4-p-tolyl-thiophen-2-yl)-3-(4-hydroxy-3,5-dimethyl-phenyl)-propan-1-one (18 mg, 48 μmol) in ethanol (1.5 mL) and 3 N aq. NaOH (0.3 mL) is treated with (S)-3-chloro-propane-1,2-diol (30 μL) and the mixture is stirred at 60° C. for 14 h. The solvent is removed in vacuo and the residue is separated on prep. TLC plates with heptane:EA 2:1 to give 3-[4-((S)-2,3-dihydroxy-propoxy)-3,5-dimethyl-phenyl]-1-(5-ethyl-4-o-tolyl-thiophen-2-yl)-propan-1-one (4 mg) as a colourless resin; LC-MS: $t_R$=1.04 min, [M+1]$^+$=453.28; $^1$H NMR (CDCl$_3$): δ 7.45 (s, 1H), 7.92-7.08 (m, 4H), 6.87 (s, 2H), 4.11-4.04 (m, 1H), 3.87-3.80 (m, 4H), 3.16-3.10 (m, 2H), 2.97-2.90 (m, 2H), 2.64 (q, J=7.6 Hz, 2H), 2.24 (s, 3H), 2.17 (s, 6H), 1.20 (t, J=7.6 Hz, 3H).

Example 21

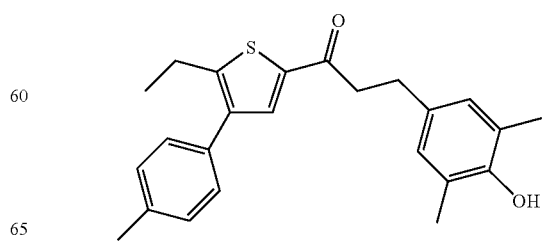

a) At 10° C., p-tolyl-acetaldehyde (11.0 g, 82 mmol) is added to a mixture of POCl$_3$ (20 mL, 230 mmol) and DMF (20 mL). The mixture is stirred at rt for 2 h before the reaction is quenched by adding water/ice and NaOAc and extracted with DCM (2×200 mL). The solvent of the organic extract is evaporated and the product is purified by CC on silica gel eluting with heptane:EA 9:1. The resulting oil (1.95 g) is dissolved in ethanol (5 mL) and then added dropwise to a freshly prepared solution of Na (370 mg, 16.2 mmol) and ethyl-2-mercaptoacetate (1.95 g, 16.2 mmol) in ethanol (20 mL). The reaction mixture is stirred at it for 72 h, diluted with water (100 mL) and extracted with EA (2×150 mL). The organic extracts are dried over MgSO$_4$ and evaporated. CC on silica gel eluting with heptane:EA 5:1 gives 4-p-tolyl-thiopene-2-carboxylic acid ethyl ester (850 mg). This ester is dissolved in ethanol (10 mL) and 3 M aq. NaOH (5 mL) and the mixture is refluxed for 2 h. The reaction mixture is acidified and extracted with DCM. The organic extract is dried over MgSO$_4$ and the solvent is evaporated to give 4-p-tolyl-thiophene-2-carboxylic acid (580 mg) as a solid; LC-MS: $t_R$=0.91 min, [M+1+CH$_3$CN]$^+$=260.16, $^1$H NMR (CDCl$_3$): δ 8.14 (s, 1H), 7.70 (s, 1H), 7.50 (d, J=7.6 Hz, 2H), 7.24 (d, J=7.6 Hz, 2H), 7.05 (s br, 1H), 2.39 (s, 3H).

b) At −70° C. a solution of 4-p-tolyl-thiophene-2-carboxylic acid (580 mg, 2.66 mmol) in THF (8 mL) is treated with tert.-BuLi (5 mL, 1.7 M solution in pentane). The mixture is stirred at −70° C. for 30 min before ethyliodide (1.2 mL) is added. The mixture is warmed to rt and stirring is continued for 72 h. The reaction is quenched by adding sat. aq. NH$_4$Cl and the mixture is extracted with DCM. The solvent of the organic extracts is evaporated and the remaining oil (780 mg) is dissolved in dry DCM (10 mL). TBTU (1.42 g, 4.43 mmol), N,O-dimethylhydroxylamine (463 mg, 4.75 mmol) and DIPEA (2 mL) is added and the mixture is stirred at rt for 18 h before it is diluted with EA and washed with water. The organic layer is separated, evaporated and the remaining residue is purified by CC on silica gel eluting with heptane:EA 4:1 to give 5-ethyl-4-p-tolyl-thiophene-2-carboxylic acid methoxy-methyl-amide (210 mg) as an oil. This oil is dissolved in THF and treated at 3° C. with methyl magnesium-bromide (0.3 mL, 3 M solution in THF). The reaction mixture is stirred at rt for 16 h before another portion of the Grignard reagent (0.5 mL) is added. Stirring is continued for 72 h. The mixture is diluted with water and extracted with EA. The solvent of the organic extract is evaporated and the crude product is purified on prep. TLC plates with heptane:EA to give 1-(5-ethyl-4-p-tolyl-thiophen-2-yl)-ethanone (28 mg) as a yellow oil; LC-MS: $t_R$=1.06 min, [M+1]$^+$=245.19.

c) A solution of 1-(5-ethyl-4-p-tolyl-thiophen-2-yl)-ethanone (28 mg, 0.115 mmol) and 3,5-dimethyl-4-hydroxybenzaldehyde (26 mg, 0.172 mmol) in ethanol (1.5 mL) and 5 N HCl in isopropanol (0.3 mL) is stirred at rt for 18 h. The solution is diluted with water and extracted with EA. The organic extract is evaporated, dissolved in methanol (3 mL) and THF (3 mL) and treated with Pd/C (30 mg, 10% Pd). The slurry is stirred under 1.5 bar of H$_2$ for 18 h. The mixture is filtered, the solvent of the filtrate is removed in vacuo and the crude product is purified by prep. HPLC to give 1-(5-ethyl-4-p-tolyl-thiophen-2-yl)-3-(4-hydroxy-3,5-dimethyl-phenyl)-propan-1-one (46 mg) as a colourless oil; LC-MS: $t_R$=1.13 min, [M+1]$^+$=379.22.

Example 22

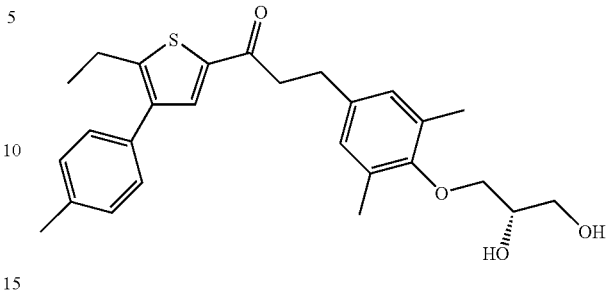

A solution of 1-(5-ethyl-4-p-tolyl-thiophen-2-yl)-3-(4-hydroxy-3,5-dimethyl-phenyl)-propan-1-one (47 mg, 0.125 mmol) in ethanol (2 mL) and 3 N aq. NaOH (0.5 mL) is treated with (S)-3-chloro-propane-1,2-diol (90 µL) and the mixture is stirred at 60° C. for 20 h. Another portion of (S)-3-chloro-propane-1,2-diol (60 µL) is added and stirring is continued at 60° C. for 5 days. The reaction mixture is diluted with water and extracted with DCM. The solvent of the organic extract is evaporated and the crude product is purified on prep. TLC plates with heptane:EA 2:1 to give 3-[4-((S)-2,3-dihydroxy-propoxy)-3,5-dimethyl-phenyl]-1-(5-ethyl-4-p-tolyl-thiophen-2-yl)-propan-1-one (6 mg) as a colourless resin; LC-MS: $t_R$=1.05 min, [M+1]$^+$=453.25; $^1$H NMR (CDCl$_3$): δ 7.56 (s, 1H), 7.30-7.21 (m, 4H), 6.88 (s, 2H), 4.11-4.05 (m, 1H), 3.87-3.80 (m, 4H), 3.18-3.11 (m, 2H), 2.98-2.85 (m, 4H), 2.39 (s, 3H), 2.25 (s, 6H), 1.29 (t, J=7.6 Hz, 3H).

Example 23

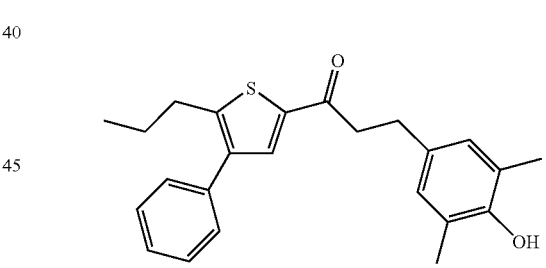

a) At −75° C., a solution of 4-phenylthiophene-2-carboxylic acid (1.20 g, 5.88 mmol) in THF (15 mL) is treated with tert.-BuLi (10 mL, 1.6 M in pentane). The mixture is stirred at −70° C. for 1 h before 1-iodopropane (1.5 mL) is added. The reaction mixture is allowed to warm to rt and is stirred overnight. The reaction is quenched with sat. aq. NH$_4$Cl (100 mL) and extracted with DCM (2×200 mL). The solvent of the organic extracts is evaporated and the residue is dissolved in DCM (15 mL). TBTU (2.03 g, 6.33 mmol), N,O-dimethylhydroxylamine (760 mg, 7.80 mmol) and DIPEA (2 mL) is added and the mixture is stirred at rt for 72 h before it is washed with water. The organic layer is separated and evaporated. The residue is purified by CC on silica gel eluting with heptane:EA 5:1 to give 4-phenyl-5-propyl-thiophene-2-carboxylic acid methoxy-methyl-amide (900 mg) as colourless oil; LC-MS: $t_R$=1.05 min, [M+1]$^+$=290.15.

b) At 2° C. methylmagnesium bromide (1 mL, 1.7 M in THF) is added to a solution of 4-phenyl-5-propyl-thiophene-2-carboxylic acid methoxy-methyl-amide (900 mg, 3.11 mmol). The mixture stirred for 1 h before another portion (0.2 mL) of the Grignard reagent is added. Stirring is continued for 2 h. The mixture is diluted with water, extracted with EA and the organic extracts are dried over $MgSO_4$ and concentrated. The crude product is purified by CC on silica gel eluting with heptane:EA 5:4 to give 1-(4-phenyl-5-propyl-thiophen-2-yl)-ethanone (456 mg) as a yellow oil; LC-MS: $t_R$=1.06 min, $[M+1]^+$=245.14, $^1$H NMR ($CDCl_3$): δ 7.59 (s, 1H), 7.47-7.32 (m, 5H), 2.87-2.81 (m, 2H), 2.54 (s, 3H), 1.76-1.63 (m, 2H), 0.95 (t, J=/.6 Hz, 3H).

c) A solution of 1-(4-phenyl-5-propyl-thiophen-2-yl)-ethanone (450 mg, 1.84 mmol) and 3,5-dimethyl-4-hydroxy-benzaldehyde (331 mg, 2.21 mmol) in ethanol (4 mL) and 5 N HCl in isopropanol (2 mL) is stirred at rt for 18 h. The dark solution is diluted with water and extracted with EA. The organic extract is evaporated, dissolved in methanol (5 mL) and THF (5 mL) and treated with Pd/C (100 mg, 10% Pd). The slurry is stirred under 1.8 bar of $H_2$ for 16 h. The mixture is filtered, the solvent of the filtrate is removed in vacuo and the crude product is purified by CC prep. TLC plates with heptane:EA 2:1 to give 3-(4-hydroxy-3,5-dimethyl-phenyl)-1-(4-phenyl-5-propyl-thiophen-2-yl)-propan-1-one (550 mg) as a colourless oil; LC-MS: $t_R$=1.13 min; $[M+1]^+$=379.20, $^1$H NMR ($CDCl_3$): δ 7.56 (s, 1H), 7.45-7.28 (m, 5H), 6.85 (s, 2H), 4.48 (s, 1H), 3.17-3.10 (m, 2H), 2.96-2.89 (m, 2H), 2.87-2.80 (m, 2H), 2.21 (s, 6H), 1.74-1.64 (m, 2H), 0.94 (t, J=7.0 Hz, 3H).

Example 24

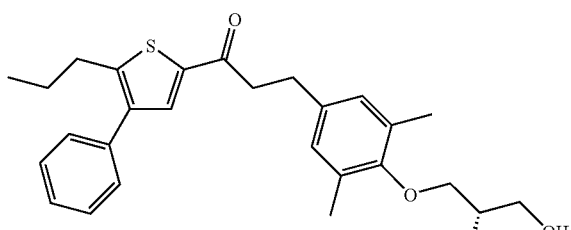

A solution of 3-(4-hydroxy-3,5-dimethyl-phenyl)-1-(4-phenyl-5-propyl-thiophen-2-yl)-propan-1-one (47 mg, 125 µmol) in isopropanol (2 mL) and 3 N aq. NaOH (0.5 mL) is treated with (S)-3-chloro-propane-1,2-diol (55 mg, 0.50 mmol) and the mixture is stirred at 70° C. for 14 h. Another portion of (S)-3-chloro-propane-1,2-diol (55 mg, 0.50 mmol) is added and stirring is continued at 70° C. for 24 h. The solvent is removed in vacuo and the residue is separated on prep. TLC plates with heptane:EA 2:1 to give 3-[4-((S)-2,3-dihydroxy-propoxy)-3,5-dimethyl-phenyl]-1-(4-phenyl-5-propyl-thiophen-2-yl)-propan-1-one (15 mg) as a colourless resin; LC-MS: $t_R$=1.05 min, $[M+1]^+$=453.18.

Example 25

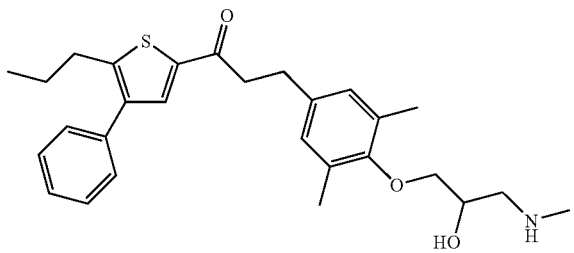

a) A solution of 3-(4-hydroxy-3,5-dimethyl-phenyl)-1-(4-phenyl-5-propyl-thiophen-2-yl)-propan-1-one (250 mg, 0.661 mmol) in 2-propanol (2 mL) and 3 N aq. NaOH (1 mL) is treated with epichlorohydrine (122 mg, 1.32 mmol) and the mixture is stirred at rt for 18 h, then diluted with water and extracted with EA. The solvent of the organic extract is evaporated to give crude 3-(3,5-dimethyl-4-oxiranylmethoxy-phenyl)-1-(4-phenyl-5-propyl-thiophen-2-yl)-propan-1-one (257 mg) as a yellow oil; LC-MS: $t_R$=1.18 min, $[M+1]^+$=435.20.

b) A solution of 3-(3,5-dimethyl-4-oxiranylmethoxy-phenyl)-1-(4-phenyl-5-propyl-thiophen-2-yl)-propan-1-one (80 mg, 191 µmol) and methylamine (0.4 µL, 2 M solution in THF) in methanol (4 mL) is stirred for 16 h at 75° C. before the solvent is evaporated. The residue is separated by prep. HPLC to give the formate salt of 3-[4-(2-hydroxy-3-methylamino-propoxy)-3,5-dimethyl-phenyl]-1-(4-phenyl-5-propyl-thiophen-2-yl)-propan-1-one (23 mg) as a colourless resin; LC-MS: $t_R$=0.91 min, $[M+1]^+$=466.27; $^1$H NMR ($CDCl_3$): δ 8.54 (s, 1H), 7.58 8s, 1H), 7.45-7.30 (m, 5H), 6.86 (s, 2H), 4.40-4.30 (m, 1H), 3.82-3.74 (m, 2H), 3.25-3.11 (m, 2H), 2.96-2.90 (m, 2H), 2.87-2.80 (m, 2H), 2.71 (s, 3H), 2.22 (s, 6H), 1.75-1.63 (m, 2H), 0.94 (t, J=7.6 Hz, 3H).

Example 26

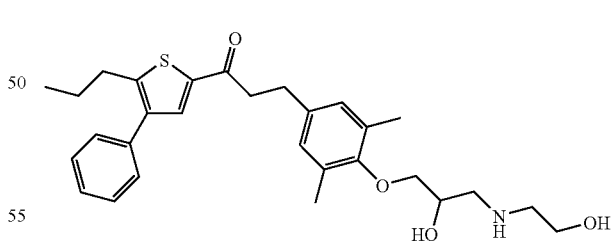

A solution of 3-(3,5-dimethyl-4-oxiranylmethoxy-phenyl)-1-(4-phenyl-5-propyl-thiophen-2-yl)-propan-1-one (80 mg, 191 µmol and aminoethanol (35 mg, 0.571 mmol) in methanol (2 mL) is stirred for 16 h at 75° C. before the solvent is evaporated. The residue is separated by prep. HPLC to give the formate salt of 3-{4-[2-hydroxy-3-(2-hydroxy-ethylamino)-propoxy]-3,5-dimethyl-phenyl}-1-(4-phenyl-5-propyl-thiophen-2-yl)-propan-1-one (27 mg) as a colourless resin; LC-MS: $t_R$=0.91 min, [M+1]$^+$=496.50.

Examples 27 to 29

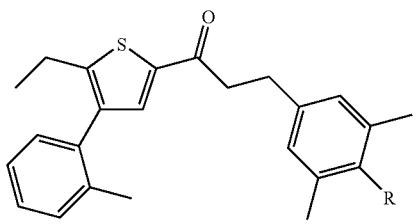

The following Examples are prepared in analogy to Example 20 starting from Example 19 and using the appropriate alkylating agent:

| Example | R | LC-MS $t_R$ (min) | [M + H]$^+$ |
|---|---|---|---|
| 27 | O-CH2-CH(OH) | 1.11 | 423.32 |
| 28 | O-CH2-CH(OH)-CH3 | 1.13 | 437.34 |
| 29 | O-CH2-CH2-N(CH3)2 | 0.95 | 450.27 |

Example 30

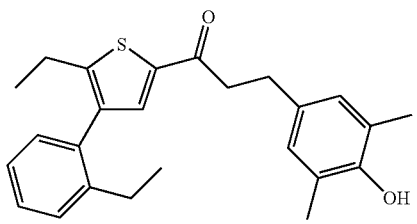

a) Over a period of 20 min a solution of SnCl$_4$ (60.9 g, 234 mmol) in hexane (20 mL) is added to a solution of 2-ethylthiophene (25 g, 223 mmol) and acetylchloride (18.4 g, 234 mmol) in hexane (80 mL). Evolving HCl gas is trapped in a NaOH solution. Evolution of HCl stops when about half of the SnCl$_4$ solution is added. The black viscous mixture is warmed to 100° C. for 30 min, before it is cooled again to rt. The mixture is poured into ice/water (600 mL), extracted with diethyl ether (3×) and the combined etheral extracts are washed with NaOH (1M), sat. NaHCO$_3$ solution and brine, dried over MgSO$_4$, filtered and evaporated. The crude 1-(5-ethyl-thiophen-2-yl)-ethanone (35 g) is added to a solution of sodium acetate (16.0 g, 195 mmol) in water (160 mL) and the resulting emulsion is stirred vigorously. To this emulsion bromine (28.5 g, 178 mmol) is added dropwise over a period of 25 min. Upon complete addition of the bromine, sodium acetate (60 g, 731 mmol) is added and the pH of the mixture is adjusted to 9 by adding 10 M aq. NaOH solution. A further portion of bromine (12.4 g, 78 mmol) is added and stirring is continued for 15 min. The reaction is quenched by adding 1 M aq. Na$_2$S$_2$O$_3$ solution and the mixture is extracted three times with diethyl ether. The organic extracts are washed with 1 N aq. NaOH, 2 N aq. HCl and brine, dried over MgSO$_4$, filtered and evaporated to give 1-(4-bromo-5-ethyl-thiophen-2-yl)-ethanone (38 g) as a brown oil; LC-MS: $t_R$=0.97 min, [M+1+CH$_3$CN]$^+$=274.20.

b) A solution of 1-(4-bromo-5-ethyl-thiophen-2-yl)-ethanone (10.6 g, 46 mmol) and 3,5-dimethyl-4-hydroxybenzaldehyde (7.6 g, 51 mmol) in ethanol (40 mL) and 5 N HCl in isopropanol (20 mL) is stirred at 50° C. for 1.5 h. The mixture is poured into ice/water (400 mL) and extracted four times with diethyl ether (100 mL). The organic extracts are washed with sat. aq. NaHCO$_3$ solution, 5% aq. citric acid solution followed by brine, dried over MgSO$_4$, filtered and evaporated. The crude product is suspended in chloroform, stirred and sonicated at rt for 15 min, filtered and dried to give 1-(4-bromo-5-ethyl-thiophen-2-yl)-3-(4-hydroxy-3,5-dimethyl-phenyl)-propenone (2.11 g) as a yellow solid; LC-MS: $t_R$=1.11 min, [M+1]$^+$=365.01; $^1$H NMR (CDCl$_3$): δ 7.74 (d, J=15.2 Hz, 1H); 7.68 (s, 1H), 7.30 (s, 2H), 7.18 (d, J=15.2 Hz, 1H), 4.99 (s, 1H), 2.84 (q, J=7.6 Hz, 2H), 2.30 (s, 6H), 1.34 (t, J=7.6 Hz, 3H).

c) A mixture of 1-(4-bromo-5-ethyl-thiophen-2-yl)-3-(4-hydroxy-3,5-dimethyl-phenyl)-propenone (2.10 g, 5.7 mmol), Pd(PPh$_3$)$_4$ (66 mg, 57 µmol), diphenylsilane (2.54 g, 13.8 mmol) and ZnCl$_2$ (627 mg, 4.6 mmol) in CHCl$_3$ (100 mL) is stirred at 40° C. for 1.5 h. The mixture is diluted with water and the organic phase is separated. The aq. phase is extracted once more with CHCl$_3$. The organic extracts are washed with 5% aq. citric acid solution, dried over MgSO$_4$, filtered and evaporated. The crude product is purified by column chromatography on silica gel eluting with heptane: EA 4:1 to give 1-(4-bromo-5-ethyl-thiophen-2-yl)-3-(4-hydroxy-3,5-dimethyl-phenyl)-propan-1-one (1.03 g) as a solid; LC-MS: $t_R$=1.08 min, [M+1]$^+$=367.18.

d) 1-(4-Bromo-5-ethyl-thiophen-2-yl)-3-(4-hydroxy-3,5-dimethyl-phenyl)-propan-1-one (45 mg, 123 µmol) and 2-ethylphenylboronic acid (22 mg, 148 µmol) are dissolved in degassed dioxane (0.8 mL) and degassed 2 M aq. Na$_2$CO$_3$ solution. To this solution PdCl$_2$(dppf) (5 mg, 7 µmol) is added under a stream of argon. The mixture is stirred at 80° C. for 8 h. The mixture is cooled to rt and an aliquot is purified by prep. HPLC to give 1-[5-ethyl-4-(2-ethyl-phenyl)-thiophen-2-yl]-3-(4-hydroxy-3,5-dimethyl-phenyl)-propan-1-one as a colourless resin; LC-MS: $t_R$=1.10 min, [M+1]$^+$=383.25.

Examples 31 to 34

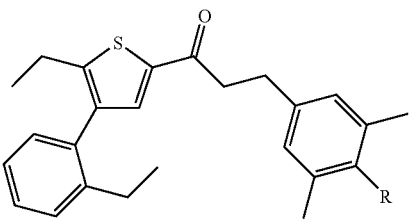

To the crude reaction mixture of Example 30 containing 1-[5-ethyl-4-(2-ethyl-phenyl)-thiophen-2-yl]-3-(4-hydroxy-3,5-dimethyl-phenyl)-propan-1-one (9.5 mg, 25 µmol) a solution of the appropriate alkylating agent (125 μmol) in isopropanol (0.15 mL) and 2 N aq. NaOH (0.15 mL) is added. The reaction mixture is stirred at 75° C. for 8 h before it is again cooled to rt. The reaction mixture is centrifuged for 15 min and the supernatant is separated by prep. HPLC to give the corresponding alkylated derivative as a colourless resin.

| Example | R | LC-MS t$_R$ (min) | [M + H]$^+$ |
|---|---|---|---|
| 31 | 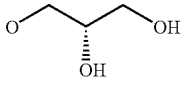 | 1.07 | 467.34 |
| 32 | 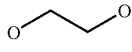 | 1.13 | 437.19 |
| 33 | 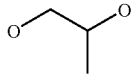 | 1.15 | 451.36 |
| 34 | 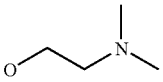 | 0.97 | 464.43 |

Examples 35 to 64

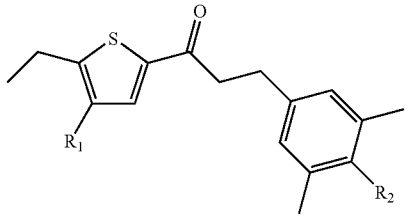

The following examples are prepared in analogy to Examples 30 and 31 to 34.

| Example | R$_1$ | R$_2$ | LC-MS t$_R$ (min) | [M + H]$^+$ |
|---|---|---|---|---|
| 35 | 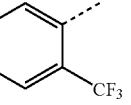 | OH | 1.12 | 433.14 |
| 36 | 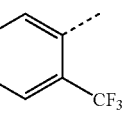 | 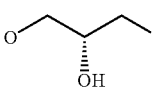 | 1.05 | 507.30 |
| 37 | 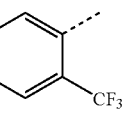 | 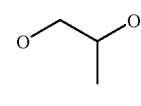 | 1.13 | 491.23 |
| 38 | 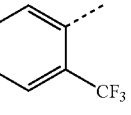 | 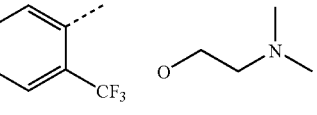 | 0.96 | 504.42 |
| 39 | 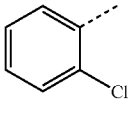 | OH | 1.12 | 399.22 |
| 40 | 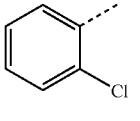 | 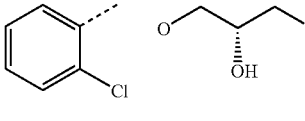 | 1.04 | 473.42 |
| 41 | 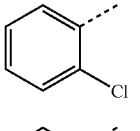 | 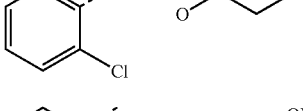 | 1.12 | 443.29 |
| 42 | 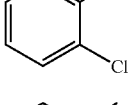 | 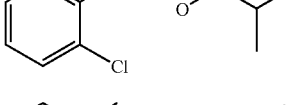 | 1.12 | 457.35 |
| 43 | 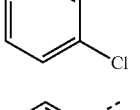 | 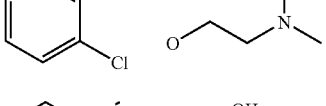 | 0.95 | 470.35 |
| 44 | 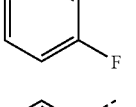 | OH | 1.10 | 383.25 |
| 45 | 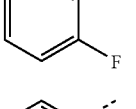 | 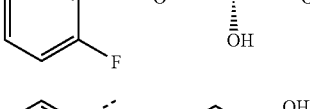 | 1.03 | 457.31 |
| 46 | 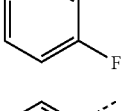 | 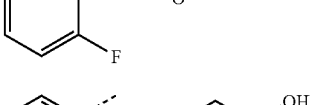 | 1.10 | 427.20 |
| 47 | 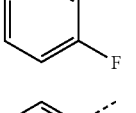 | 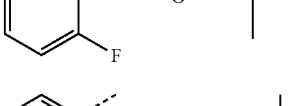 | 1.11 | 441.27 |
| 48 | 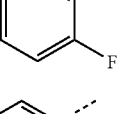 | 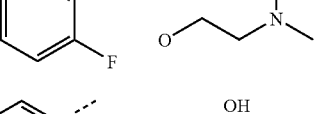 | 0.94 | 454.41 |
| 49 | 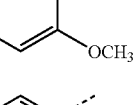 | OH | 1.10 | 395.28 |
| 50 | 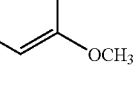 |  | 1.03 | 469.25 |

| Example | R₁ | R₂ | $t_R$ (min) | $[M+H]^+$ |
|---|---|---|---|---|
| 51 | 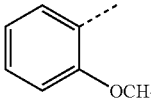 | 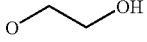 | 1.09 | 439.37 |
| 52 | 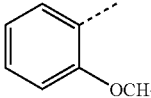 | 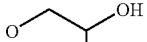 | 1.10 | 453.39 |
| 53 | 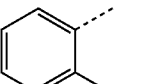 |  | 0.93 | 466.32 |
| 54 | 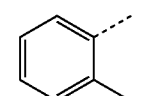 | OH | 1.14 | 393.37 |
| 55 |  | 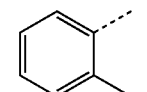 | 1.07 | 467.29 |
| 56 | 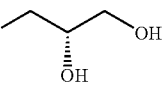 | 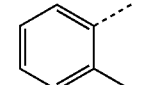 | 1.13 | 437.43 |
| 57 | 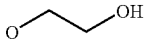 | 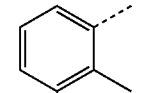 | 1.15 | 451.28 |
| 58 | 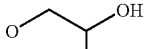 | 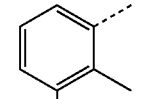 | 0.97 | 464.36 |
| 59 |  | 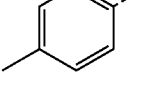 | 1.12 | 423.27 |
| 60 | 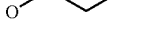 | 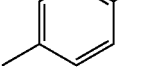 | 1.14 | 437.31 |
| 61 |  | OH | 1.13 | 379.30 |
| 62 | 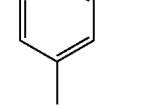 |  | 1.11 | 423.32 |
| 63 | 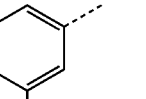 | 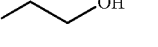 | 1.14 | 437.36 |
| 64 | 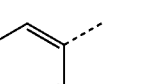 | OH | 0.87 | 366.34 |

Example 65

GTPγS Assay to Determine $EC_{50}$ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM $MgCl_2$ (Fluka, 63064), 0.1% BSA (Calbiochem, 126609), 1 µM GDP (Sigma, G-7127), 2.5% DMSO (Fluka, 41644), 50 µM $^{35}$S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of $^{35}$S-GTPγS. After addition of 50 µl of $^{35}$S-GTPγS, the assay is incubated for 1 h at room temperature.

The assay is terminated by transfer of the reaction mixture to a Multiscreen plate (Millipore, MAHFC1H60) using a cell harvester from Packard Biosciences, and the plates are washed with ice-cold 10 mM $Na_2HPO_4/NaH_2PO_4$ (70%/30%), dried, sealed at the bottom and, after addition of 25 µl MicroScint20 (Packard Biosciences, order no. 6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay.

Table 1 shows the $EC_{50}$ value of some compounds of the Examples. The $EC_{50}$ values were determined according to the method described above:

TABLE 1

| Compound of Example | $EC_{50}$ [nM] |
|---|---|
| 10 | 6.7 |
| 11 | 18.3 |

TABLE 1-continued

| Compound of Example | EC$_{50}$ [nM] |
|---|---|
| 20 | 6.3 |
| 24 | 16.4 |
| 31 | 9.3 |
| 50 | 11.5 |

Example 66

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 3 h after oral administration of 10 mg/kg of a compound of the present invention to normotensive male Wistar rats as compared to a group of animals treated with vehicle only.

TABLE 2

| Compound of Example | Lymphocyte counts |
|---|---|
| 10 | −48.5% |

The invention claimed is:
1. A compound selected from the group consisting of thiophenes of the Formula (I),

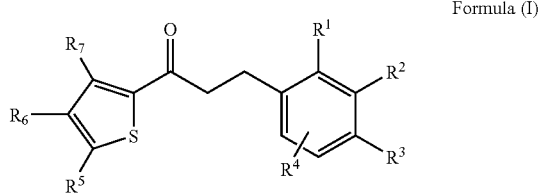

Formula (I)

wherein
R$^1$ represents hydrogen, lower alkyl, lower alkoxy, or halogen;
R$^2$ represents hydrogen, lower alkyl, lower alkoxy, or halogen;
R$^3$ represents hydrogen, hydroxy-lower alkyl, 2,3-dihydroxypropyl, di-(hydroxy-lower alkyl)-lower alkyl, —CH$_2$—(CH$_2$)$_k$—NR$^{31}$R$^{32}$, (azetidine-3-carboxylic acid)-1-yl-methyl, (azetidine-3-carboxylic acid lower alkylester)-1-yl-methyl, 2-[(azetidine-3-carboxylic acid)-1-yl]-ethyl, 2-[(azetidine-3-carboxylic acid lower alkylester)-1-yl]-ethyl, 3-[(azetidine-3-carboxylic acid)-1-yl]-propyl, 3-[(azetidine-3-carboxylic acid lower alkylester)-1-yl]-propyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, 2-[(pyrrolidine-3-carboxylic acid)-1-yl]-ethyl, 2-[(pyrrolidine-3-carboxylic acid lower alkylester)-1-yl]-ethyl, 2-[(pyrrolidine-2-carboxylic acid)-1-yl]-ethyl, 2-[(pyrrolidine-2-carboxylic acid lower alkylester)-1-yl]-ethyl, 3-[(pyrrolidine-3-carboxylic acid)-1-yl]-propyl, 3-[(pyrrolidine-3-carboxylic acid lower alkylester)-1-yl]-propyl, 3-[(pyrrolidine-2-carboxylic acid)-1-yl]-propyl, 3-[(pyrrolidine-2-carboxylic acid lower alkylester)-1-yl]-propyl, —CH$_2$—(CH$_2$)$_n$—CONR$^{31}$R$^{32}$, —CO—NHR$^{31}$, 1-(1-(3-carboxy-azetidinyl))-2acetyl, 1-(-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$—CH(OH)—CH$_2$—NR$^{31}$R$^{32}$, hydroxy, lower alkoxy, fluoro-lower alkoxy, hydroxy-lower alkoxy, di-(hydroxy-lower alkyl)-lower alkoxy, 1-glyceryl, 2-glyceryl, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(lower alkyl)-piperazin-1-yl]-ethoxy, 2-[(4-(2hydroxy-ethyl)-piperazin-1-yl]-ethoxy, 3-piperazin-1-yl-propoxy, 3-[4-(lower alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]ethoxy, 2-[(pyrrolidine-2-carboxylic acid)-1-yl]-ethoxy, 2-[(pyrrolidine-2-carboxylic acid lower alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)-1-yl]-propoxy, 3-[(3-hydroxy-pyrrolidine)-1-yl]-propoxy, 2-amino-3-hydroxy-2-hydroxymethyl-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-(lower alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-ylpropoxy, 2-hydroxy-3-[(lower alkyl)-piperazin-1yl]-propoxy, 2-hydroxy-3-[(4(2-hydroxy-ethyl)-piperazin-1-yl]-propoxy, 2-hydroxy-3-morpholin-4-yl-propoxy, —$NR^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—NHCO$R^{34}$, —$(CH_2)_n$CH(OH)—$CH_2$—NHCO$R^{34}$, —$OCH_2$—$(CH_2)_m$—NHCO$R^{34}$, —$OCH_2$—CH(OH)—$CH_2$—NHCO$R^{34}$;

$R^{31}$ represents hydrogen, methyl, ethyl, 1-propyl, 2-propyl, 2-hydroxyethyl, 2-hydroxy- 1-hydroxymethyl-ethyl, 2-lower alkoxyethyl, 3-hydroxypropyl, 3-lower alkoxypropyl, 2-aminoethyl, 2-(lower alkylamino) ethyl, 2-(di-(lower alkyl)amino)ethyl, carboxymethyl, lower alkylcarboxymethyl, 2-carboxyethyl, or 2-(lower alkylcarboxy)ethyl;

$R^{32}$ represents hydrogen or methyl;

$R^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

$R^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents the integer 0, 1, or 2;

$R^4$ represents hydrogen, lower alkyl or halogen;

$R^5$ represents trifluoromethyl, methyl, ethyl, or propyl;

$R^6$ represents phenyl optionally mono- or di-substituted, wherein the substituents are independently selected from methyl, ethyl, trifluoromethyl, halogen and methoxy; or 2-, 3- or 4-pyridyl optionally substituted with methyl or methoxy; and $R^7$ represents hydrogen, or methyl;

in free or salt form.

2. The compound according to claim 1, wherein $R^1$ and $R^4$ represent hydrogen, and $R^2$ represents a methyl group.

3. The compound according to claim 1, wherein $R^1$ represents hydrogen, and $R^2$ and $R^4$ represent a methyl group, wherein $R^4$ is in the ortho-position with respect to $R^3$.

4. The compound according to claim 1, wherein $R^1$ represents hydrogen, $R^2$ represents a methyl group, and $R^4$ represents an ethyl group in the ortho-position with respect to $R^3$.

5. The compound according to claim 1, wherein $R^1$ represents hydrogen, $R^2$ represents a methyl group, and $R^4$ represents chlorine in the ortho-position with respect to $R^3$.

6. The compound according to claim 1, wherein $R^1$ and $R^4$ represent hydrogen, and $R^2$ represents chlorine.

7. The compound according to claim 1, wherein $R^1$ represents hydrogen, $R^2$ represents a methoxy group, and $R^4$ represents a chlorine or fluorine in the ortho-position with respect to $R^3$.

8. The compound according to claim 1, wherein $R^1$ represents a methoxy group, and $R^2$ and $R^4$ represent hydrogen.

9. The compound according to claim 1, wherein $R^3$ represents hydrogen, hydroxy-lower alkyl, 2,3-dihydroxypropyl, di-(hydroxy-lower alkyl)-lower alkyl, (azetidine-3-carboxylic acid)-1-yl-methyl, (azetidine-3-carboxylic acid lower alkylester)-1-yl-methyl, (pyrrolidine-3-carboxylic acid)-1-yl-methyl, (pyrrolidine-3-carboxylic acid lower alkylester)-1-yl-methyl, (pyrrolidine-2-carboxylic acid)-1-yl-methyl, (pyrrolidine-2-carboxylic acid lower alkylester)-1-yl-methyl, —$CH_2$—$(CH_2)_n$—CON$R^{31}R^{32}$, —CO—NH$R^{31}$, —$(CH_2)_n$CH(OH)—$CH_2$—N$R^{31}R^{32}$, lower alkoxy, hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH_2)_m$—N$R^{31}R^{32}$, 2-[azetidine-3-carboxylic acid)-1-yl]-ethoxy, 2-[(azetidine-3-carboxylic acid lower alkylester)-1-yl]-ethoxy, 2-[(pyrrolidine-3-carboxylic acid)-1-yl]-ethoxy, 2-[(pyrrolidine-3-carboxylic acid lower alkylester)-1-yl]-ethoxy, 2-[(pyrrolidine-2-carboxylic acid)-1-yl]-ethoxy, 2-[(pyrrolidine-2-carboxylic acid lower alkylester)- 1-yl]-ethoxy, 2-[(2-hydroxy-pyrrolidine)- 1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid lower alkylester)-1-yl]-propoxy, 3-[(pyrrolidine-3-carboxylic acid)-1-yl]-propoxy, 3-[(pyrrolidine-3-carboxylic acid lower alkylester)-1-yl]-propoxy, 3-[(pyrrolidine-2-carboxylic acid)-1-yl]-propoxy, 3-[(pyrrolidine-2-carboxylic acid lower alkylester)-1-yl]-propoxy, 3-[(2-hydroxy-pyrrolidine)- 1-yl]-propoxy, 3-[(3-hydroxy-pyrrolidine)- 1-yl]-propoxy, 2-amino-3-hydroxy-2-hydroxymethyl-propoxy, —O—$CH_2$—CON$R^{31}R^{32}$, —$OCH_2$—CH(OH)-$CH_2$—N$R^{31}R^{32}$, 3-[(azetidine-3-carboxylic acid)-1-yl]-2-hydroxypropoxy, 3-[(azetidine-3-carboxylic acid lower alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid lower alkylester)-1-yl]-propoxy, 2-hydroxy-3-[(pyrrolidine-2-carboxylic acid)- 1-yl]-propoxy, 2-hydroxy-3-[(pyrrolidine-2-carboxylic acid lower alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(lower alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —N$R^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$—$NHSO_2R^{33}$, —$OCH_2$—CH(OH)—$CH_2$—$NHSO_2R^{33}$, —$CH_2$—$(CH_2)_k$—NHCO$R^{34}$, —$(CH_2)_n$CH(OH)—$CH_2$—NHCO$R^{34}$, —$OCH_2$—$(CH_2)_m$—NHCO$R^{34}$, —$OCH_2$—CH(OH)—$CH_2$—NHCO$R^{34}$, wherein $R^{31}$, $R^{32}$, $R^{33}$ and $R^{34}$ are as defined in claim 1.

10. The compound according to claim 1, wherein $R^3$ represents hydroxy-lower alkyl, 2,3-dihydroxypropyl, di-(hydroxy-lower alkyl)-lower alkyl, (azetidine-3-carboxylic acid)-1-yl-methyl, —CO—NH$R^{31}$, —$(CH_2)_n$CH(OH)—$CH_2$-N$R^{31}R^{32}$, lower alkoxy, hydroxy-lower alkoxy, di-(hydroxy-lower alkyl)-lower alkoxy, 1-glyceryl, 2-glyceryl, 2-hydroxy-3-methoxy-propoxy, —$OCH_2$—$(CH2)_m$—N$R^{31}R^{32}$, 2-amino-3-hydroxy-2-hydroxymethyl-propoxy, —O—$CH_2$—CON$R^{31}R^{32}$, —$OCH_2$—CH(OH)—$CH_2$—N$R^{31}R^{32}$, —N$R^{31}R^{32}$, —NHCO—$R^{31}$, —$CH_2$—$(CH_2)_k$—$NHSO_2R^{33}$, —$(CH_2)_n$CH(OH)—$CH_2$—$NHSO_2R^{33}$, —$OCH_2$—$(CH_2)_m$, —$NHSO_2R^{33}$, —$OCH_2$—CH(OH)—$CH_2$—$NHSO_2R^{33}$, —$CH_2$—$(CH_2)_k$—NHCO$R^{34}$, —$(CH_2)_n$CH(OH)—$CH_2$—NHCO$R^{34}$, —$OCH_2$—$(CH_2)_m$—NHCO$R^{34}$, or —$OCH_2$—CH(OH)—$CH_2$—NHCO$R^{34}$, wherein $R^{31}$, $R^{32}$, $R^{33}$ and $R^{34}$ are as defined in claim 1.

11. The compound according to claim 1, wherein $R^3$ represents hydroxy-lower alkyl, 2,3-dihydroxypropyl, di-(hydroxy-lower alkyl)-lower alkyl, —CO—NH$R^{31}$, lower alkoxy, hydroxy-lower alkoxy, di-(hydroxy-lower alkyl)-lower alkoxy, 1-glyceryl, 2-glyceryl, 2-hydroxy-3-methoxy-propoxy, or —O—$CH_2$—CON$R^{31}R^{32}$, wherein $R^{31}$ and $R^{32}$ are as defined in claim 1.

12. The compound according to claim 1, wherein $R^5$ represents ethyl.

13. The compound according to claim 1, wherein $R^6$ represents an unsubstituted phenyl ring.

14. The compound according to claim 1, wherein $R^7$ represents hydrogen.

15. The compound according to claim 1 selected from the group consisting of:
- 3-[4-((S)-2,3-dihydroxy-propoxy)-3,5-dimethyl-phenyl]-1-(5-ethyl-4-phenyl-thiophen-2-yl)-propan-1-one,
- 3-[4-((S)-2,3-dihydroxy-propoxy)-3,5-dimethyl-phenyl]-1-(5-ethyl-4-(2-methyl-phenyl)-thiophen-2-yl)-propan-1-one, and
- 3-[4-((S)-2,3-dihydroxy-propoxy)-3,5-dimethyl-phenyl]-1-(1-(4-phenyl-5-propyl-thiophen-2-yl)-propan-1-one.

16. A pharmaceutical composition comprising a compound according to claim 1, in free or pharmaceutically acceptable salt form, and a pharmaceutically acceptable carrier.

* * * * *